(12) United States Patent
Ando

(10) Patent No.: US 10,508,994 B2
(45) Date of Patent: Dec. 17, 2019

(54) IMAGE INSPECTION APPARATUS AND IMAGE INSPECTION METHOD

(71) Applicant: Keyence Corporation, Osaka (JP)

(72) Inventor: Daisuke Ando, Osaka (JP)

(73) Assignee: Keyence Corporation, Osaka (JP)

( * ) Notice: Subject to any disclaimer, the term of this patent is extended or adjusted under 35 U.S.C. 154(b) by 0 days.

(21) Appl. No.: 15/955,735

(22) Filed: Apr. 18, 2018

(65) Prior Publication Data

US 2018/0348144 A1 Dec. 6, 2018

(30) Foreign Application Priority Data

May 31, 2017 (JP) .................................. 2017-108095

(51) Int. Cl.
*G01N 21/88* (2006.01)
*G01N 21/55* (2014.01)
(Continued)

(52) U.S. Cl.
CPC ......... *G01N 21/8803* (2013.01); *G01N 21/01* (2013.01); *G01N 21/55* (2013.01);
(Continued)

(58) Field of Classification Search
CPC ............ G01B 11/2527; G01B 11/2513; G01N 21/8806; G01N 21/8851; G01N 21/898;
(Continued)

(56) References Cited

U.S. PATENT DOCUMENTS 6,661,912 B1 * 12/2003 Taguchi ........... G01N 21/95607
356/237.2
8,705,049 B2 * 4/2014 Honma .............. G01B 11/2527
356/601
(Continued)

FOREIGN PATENT DOCUMENTS

JP 2001-174414 A 6/2001
JP 2009-243920 A 10/2009

OTHER PUBLICATIONS

U.S. Appl. No. 15/957,937, filed Apr. 20, 2018 (129 pages).
(Continued)

*Primary Examiner* — Sang H Nguyen
(74) *Attorney, Agent, or Firm* — Kilyk & Bowersox, P.L.L.C.

(57) ABSTRACT

An image inspection apparatus includes an illuminating section for irradiating illumination light, a line camera in which a plurality of imaging elements are arrayed to be linearly arranged, the line camera receiving the light irradiated from the illuminating section and reflected on the inspection target object, a display section for displaying an image captured by the line camera, an optical axis adjusting section for adjusting an optical axis of the line camera, a trigger setting section for specifying a trigger that specifies timing when the inspection target object is imaged by the line camera, an aspect ratio adjusting section for adjusting longitudinal and lateral pixel resolutions of the image captured by the line camera, and a display control section for displaying the optical axis adjusting section, the trigger
(Continued)

setting section, and the aspect ratio adjusting section on the display section in order.

5 Claims, 29 Drawing Sheets

(51) Int. Cl.
 *G01N 21/01* (2006.01)
 *H04N 7/12* (2006.01)
 *G06T 7/00* (2017.01)

(52) U.S. Cl.
 CPC ..... *G01N 21/8806* (2013.01); *G01N 21/8851* (2013.01); *G06T 7/0004* (2013.01); *H04N 7/125* (2013.01); *G01N 2021/0181* (2013.01); *G01N 2021/8812* (2013.01); *G01N 2021/8887* (2013.01)

(58) Field of Classification Search
 CPC ....... G01N 2021/8816; G01N 21/8803; G01N 21/01; G01N 21/55; G06T 7/0002; G06T 2207/30108; G06T 2207/30164; G06T 2207/10152; G06T 7/0004; H04N 7/125
 See application file for complete search history.

(56) References Cited

U.S. PATENT DOCUMENTS

| 9,819,872 B2* | 11/2017 | Yoshikawa | H04N 5/2353 |
| 9,959,451 B2* | 5/2018 | Suenaga | G06K 9/00208 |
| 2003/0086008 A1* | 5/2003 | Nagano | H04N 9/045 348/272 |
| 2007/0206940 A1* | 9/2007 | Kusaka | G03B 13/28 396/128 |
| 2007/0223802 A1* | 9/2007 | Tateda | B29C 70/54 382/141 |
| 2007/0247614 A1* | 10/2007 | Puah | H05K 13/0813 356/73 |
| 2009/0274370 A1* | 11/2009 | Sakamoto | G06K 9/00624 382/190 |
| 2010/0246326 A1* | 9/2010 | Ichigo | G01N 29/12 367/93 |
| 2011/0037888 A1* | 2/2011 | Onuki | G02B 7/346 348/340 |
| 2017/0011502 A1* | 1/2017 | Kobayashi | G06T 7/0004 |
| 2018/0106593 A1* | 4/2018 | Arden | H04N 5/232 |

OTHER PUBLICATIONS

U.S. Appl. No. 15/955,732, filed Apr. 18, 2018 (218 pages).
U.S. Appl. No. 15/956,775, filed Apr. 19, 2018 (215 pages).
U.S. Appl. No. 15/957,938, filed Apr. 20, 2018 (217 pages).

* cited by examiner

FIG. 6A
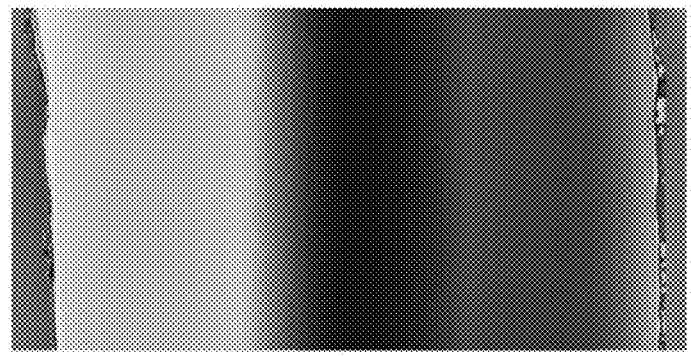
FIG. 6B ↓ DIFFERENCE
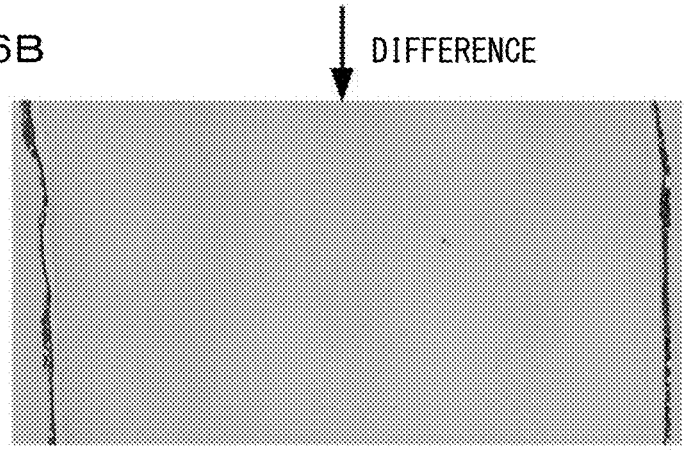
FIG. 7A
FIG. 7B

FIG. 12A
FIG. 12B
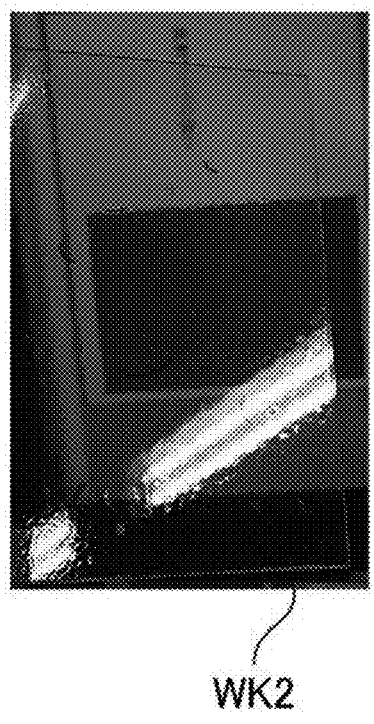
WK2
FIG. 13A
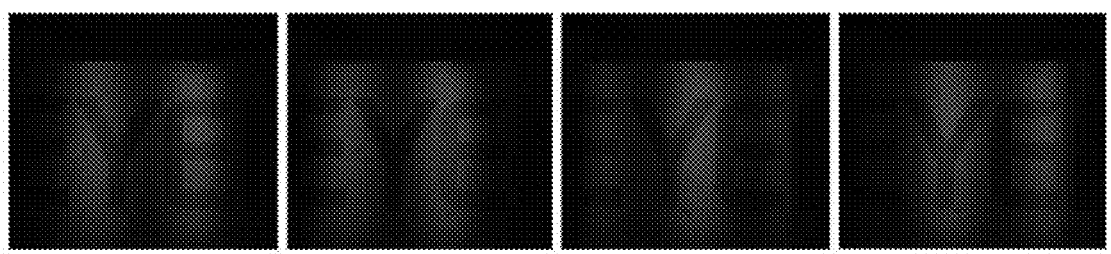
FIG. 13B
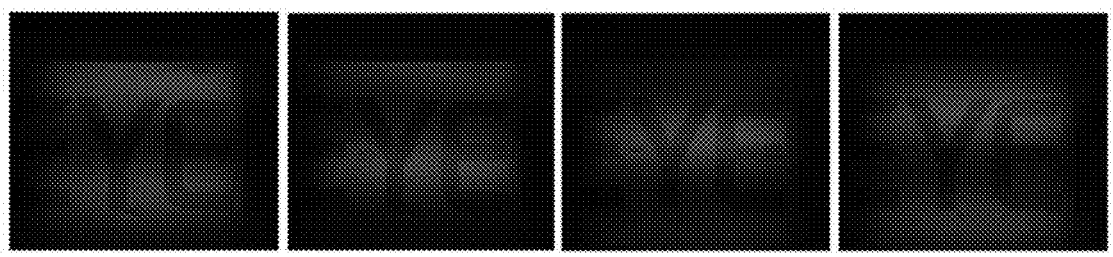

FIG. 15
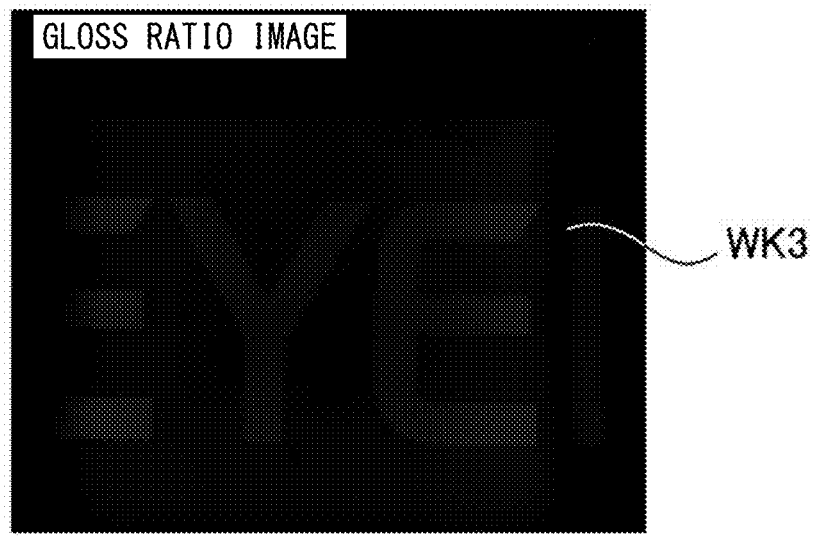
FIG. 16A
FIG. 16B
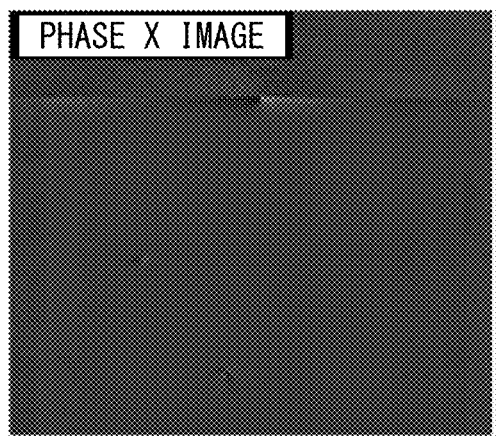
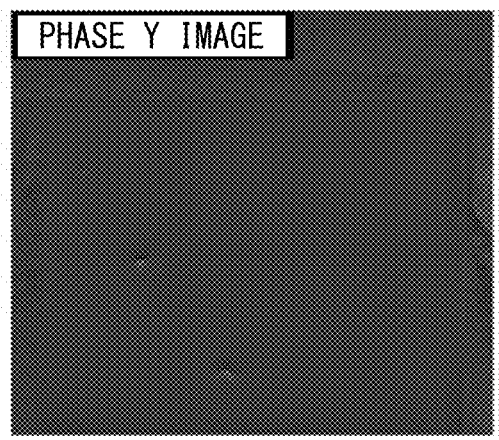

IMAGE INSPECTION APPARATUS AND IMAGE INSPECTION METHOD

CROSS-REFERENCE TO RELATED APPLICATIONS

The present application claims foreign priority based on Japanese Patent Application No. 2017-108095, filed May 31, 2017, the contents of which is incorporated herein by reference.

BACKGROUND OF THE INVENTION

1. Field of the Invention

The present invention relates to an image inspection apparatus and an image inspection method.

2. Description of Related Art

There has been known an image inspection apparatus that irradiates light on the surface of work (an inspection target object or a subject) from an illuminating section, receives reflected light with an imaging section, analyzes a luminance distribution of the received light, and detects a flaw and the like present in the work. In the image inspection apparatus, the positions and the angles of the illuminating section and the imaging section need to be adjusted to be optimum during setting such that an image of the work can be correctly captured. After the setting, the positions and the angles need to be periodically confirmed to determine whether deviation due to aged deterioration, an unintended contact, or the like is present. If there is deviation, the positions and the angles need to be adjusted.

As the imaging section, besides an area camera in which imaging elements are two-dimensionally arranged, a line camera in which imaging elements are arrayed along a width direction orthogonal to a moving direction of work is used. The line camera is capable of, for example, while moving belt-like work or rotating columnar work, continuously inspecting the surface of the work.

However, the method of detecting inclination of the camera on the basis of an image obtained by imaging the pattern for angle adjustment is a method of setting the camera and the illuminating section in an inspection environment of a user, causing the camera to image the pattern, and finely adjusting a camera angle. Therefore, in this method, measures against occurrence of inclination in the camera due to aged deterioration or the like are not taken. As a result, an inspection failure is easily caused.

JP-A-2001-174414 (Patent Literature 1) and JP-A-2009-243920 (Patent Literature 2) are examples of the related art.

SUMMARY OF THE INVENTION

The present invention has been devised in view of such a background, and an object of the present invention is to provide an image inspection apparatus, an image inspection method, an image inspection program, and a computer-readable recording medium or a device having the image inspection program recorded therein that make it possible to easily perform setting work for a camera section and an illuminating section in an inspection performed using image processing.

An image inspection apparatus according to a first aspect of the present invention is an image inspection apparatus for performing a visual inspection of an inspection target object. The image inspection apparatus includes: an illuminating section for irradiating illumination light on the inspection target object; a line camera in which a plurality of imaging elements are arrayed to be linearly arranged, the line camera receiving the light irradiated from the illuminating section and reflected on the inspection target object; a display section for displaying an image captured by the line camera; an optical axis adjusting section for adjusting an optical axis of the line camera in a state in which an image obtained by imaging the inspection target object in a standstill state with the line camera is displayed on the display section; a trigger setting section for specifying a trigger that specifies timing when the inspection target object is imaged by the line camera; an aspect ratio adjusting section for adjusting longitudinal and lateral pixel resolutions of the image captured by the line camera; and a display control section for displaying the optical axis adjusting section, the trigger setting section, and the aspect ratio adjusting section on the display section in order. With the configuration explained above, it is possible to easily perform troublesome setting work for imaging conditions such as optical axis adjustment of the line camera and adjusting of an aspect ratio.

According to a second aspect, in addition to the configuration explained above, in the image inspection apparatus, the aspect ratio adjusting section can include: a pixel resolution calculating section configured to calculate pixel resolutions in a longitudinal direction and a lateral direction of the image captured by the line camera; and an imaging parameter adjusting section for adjusting imaging parameters that define imaging conditions of the line camera.

Further, according to a third aspect, in addition to one of the configurations explained above, in the image inspection apparatus, the aspect ratio adjusting section can include a longitudinal direction expansion and contraction section for expanding and contracting, in the longitudinal direction, the image obtained by the imaging of the line camera.

Furthermore, according to a fourth aspect, in addition to any one of the configurations explained above, in the image inspection apparatus, the optical axis adjusting section can be capable of adjusting an optical axis of the illuminating section.

Furthermore, according to a fifth aspect, in addition to any one of the configurations explained above, in the image inspection apparatus, the aspect ratio adjusting section includes an interval adjusting section for adjusting an imaging interval of the line camera.

Furthermore, an image inspection apparatus according to a sixth aspect is an image inspection apparatus for performing a visual inspection of an inspection target object. The image inspection apparatus includes: an illuminating section for irradiating illumination light on the inspection target object; a line camera in which a plurality of imaging elements are arrayed to be linearly arranged, the line camera receiving the light irradiated from the illuminating section and reflected on the inspection target object; an image-for-optical-axis-adjustment generating section configured to repeatedly capture, with the line camera, images of an inspection target object for optical axis adjustment in a standstill state during inspection setting to generate an image for optical axis adjustment having periodicity in a line direction of the line camera; a display section for displaying the image for optical axis adjustment generated by the image-for-optical-axis-adjustment generating section; an image-for-pixel-resolution-calculation generating section for, after optical axis adjustment of the line camera is performed on the basis of the image for optical axis adjustment displayed on the display section, repeatedly capturing images with the line camera while moving, in one direction, a pattern for pixel resolution calculation having a known dimension to generate an image for pixel resolution calculation; a measurement position designating section for receiving designation of a dimension measurement part on the image for pixel resolution calculation displayed on the display section; a measuring section for measuring a dimension of the measurement part designated by the measurement position designating section; a dimension input section for receiving an input of an actual dimension of the measurement part from a user; a pixel resolution calculation parameter setting section configured to set, as a pixel resolution calculation parameter, a ratio of the dimension measured by the measuring section and the actual dimension input to the dimension input section; an interval adjusting section for adjusting an imaging interval of the line camera according to the pixel resolution calculation parameter set by the pixel resolution calculation parameter setting section; and an image-for-inspection generating section for repeating the imaging at the imaging interval adjusted by the interval adjusting section to generate an image for inspection. With the configuration explained above, it is possible to easily perform troublesome setting work for imaging conditions of the line camera.

Furthermore, according to a seventh aspect, in addition to any one of the configurations explained above, in the image inspection apparatus, the pattern for pixel resolution calculation can be a pattern formed by alternately displaying square white and black patterns in a checkered shape.

Furthermore, according to an eighth aspect, in addition to any one of the configurations explained above, in the image inspection apparatus, the interval adjusting section can be configured to receive an imaging interval manually adjusted by a user. With the configuration explained above, the user can adjust the imaging interval while referring to the image for optical axis adjustment and the like displayed on the display section.

Furthermore, according to a ninth aspect, in addition to any one of the configurations explained above, in the image inspection apparatus, the interval adjusting section can be configured to automatically calculate the imaging interval of the line camera with image processing according to the pixel resolution calculation parameter set by the pixel resolution calculation parameter setting section. With the configuration explained above, it is possible to automatically perform, with the image processing, troublesome setting of the imaging interval of the line camera.

Furthermore, according to a tenth aspect, in addition to any one of the configurations explained above, in the image inspection apparatus, the interval adjusting section can be configured to adjust the imaging interval of the line camera to set longitudinal and lateral pixel resolutions of the image for inspection generated by the image-for-inspection generating section to 1:1. With the configuration explained above, it is possible to adjust the imaging conditions to match the longitudinal and lateral pixel resolutions and accurately perform the visual inspection.

Furthermore, according to an eleventh aspect, in addition to any one of the configurations explained above, in the image inspection apparatus, the line camera can be provided separately from the illuminating section.

Furthermore, according to a twelfth aspect, in addition to any one of the configurations explained above, the image inspection apparatus can further include: a light-condensing optical system configured to condense reflected light of the illumination light irradiated on the inspection target object from the illuminating section and reflected on the inspection target object; and an imaging inclination sensor added to the line camera and capable of outputting, when a direction parallel to an optical axis of the light-condensing optical system is represented as a Z axis, a direction orthogonal to the Z axis and parallel to an arranging direction of the imaging elements is represented as an X axis, and a direction orthogonal to the X axis and the Z axis is represented as a Y axis, values indicating inclinations of the X axis, the Y axis, and the Z axis of the line camera with respect to a horizontal direction or a gravity direction. The image inspection apparatus can be configured to cause, on the basis of the values indicating the inclinations output from the imaging inclination sensor, the display section to display figures or values indicating degrees of at least any two inclinations among the inclinations of the X axis, the Y axis, and the Z axis of the line camera.

Furthermore, according to a thirteenth aspect, in addition to any one of the configurations explained above, in the image inspection apparatus, the line camera can be disposed in a position where specular reflection light of the inspection target object is received and configured to generate a shape image of the inspection target object on the basis of a deflectometry principle.

Furthermore, an image inspection method according to a fourteenth aspect is an image inspection method for performing a visual inspection of an inspection target object. The image inspection method includes: irradiating illumination light on an inspection target object for optical axis adjustment in a standstill state, imaging, with a line camera in which a plurality of imaging elements are arrayed to be linearly arranged, the light reflected on the inspection target object, and causing a display section to display a captured image; urging a user to adjust an optical axis of the line camera in a state in which the image is displayed on the display section; urging the user to specify a trigger that specifies timing when the inspection target object is imaged by the line camera; and urging the user to adjust longitudinal and lateral pixel resolutions of the image captured by the line camera. With the configuration explained above, it is possible to easily perform troublesome setting work for imaging conditions such as optical axis adjustment of the line camera and adjustment of an aspect ratio.

Furthermore, according to a fifteenth aspect, in addition to any one of the configurations explained above, in the image inspection method, the urging the user to adjust the pixel resolutions can include: calculating pixel resolutions in a longitudinal direction and a lateral direction of the image captured by the line camera; and calculating an imaging interval for setting the calculated pixel resolutions in the longitudinal direction and the lateral direction to a desired ratio and reflecting the imaging interval on imaging parameters.

Furthermore, according to a sixteenth aspect, in addition to any one of the configurations explained above, in the image inspection method, the urging the user to adjust the pixel resolutions can include changing the imaging interval of the line camera to bring the pixel resolution in the longitudinal direction close to the pixel resolution in the lateral direction.

Furthermore, an image inspection method according to a seventeenth aspect is an image inspection method for performing a visual inspection of an inspection target object. The image inspection method includes: setting an inspection target object for optical axis adjustment during inspection setting to a standstill state, irradiating illumination light on the inspection target object, repeatedly imaging, with a line camera in which a plurality of imaging elements are arrayed to be linearly arranged, the light reflected on the inspection target object, generating an image for optical axis adjustment having periodicity in a line direction of the line camera, and causing a display section to display the image for optical axis adjustment; urging a user to adjust an optical axis of the line camera on the basis of the image for optical axis adjustment displayed on the display section; setting a pattern for pixel resolution calculation having a known dimension as the inspection target object, repeatedly capturing images with the line camera while moving the pattern for pixel resolution calculation in one direction to generate an image for pixel resolution calculation; receiving designation of a dimension measurement part on the image for pixel resolution calculation displayed on the display section; measuring a dimension of the designated measurement part; receiving an input of an actual dimension of the measurement part from the user and setting, as a pixel resolution calculation parameter, a ratio of the measured dimension and the input actual dimension; adjusting an imaging interval of the line camera according to the set pixel resolution calculation parameter; and repeating the imaging at the adjusted imaging interval to generate an image for inspection. With the configuration explained above, it is possible to easily perform troublesome setting work for imaging conditions of the line camera.

Furthermore, an image inspection program according to an eighteenth aspect is an image inspection program for performing a visual inspection of an inspection target object. The image inspection program causes a computer to realize: a function of irradiating illumination light on an inspection target object for optical axis adjustment in a standstill state, imaging, with a line camera in which a plurality of imaging elements are arrayed to be linearly arranged, the light reflected on the inspection target object, and causing a display section to display a captured image; a function of urging a user to adjust an optical axis of the line camera in a state in which the image is displayed on the display section; a function of urging the user to specify a trigger that specifies timing when the inspection target object is imaged by the line camera; a function of urging the user to adjust longitudinal and lateral pixel resolutions of the image captured by the line camera; and a guidance function of urging, with the optical axis adjusting function, the trigger specifying function, and the pixel resolution adjusting function, the user to sequentially set imaging conditions for the inspection target object by the line camera for each of parameters configuring the imaging conditions. With the configuration explained above, it is possible to easily perform troublesome setting work for imaging conditions such as optical axis adjustment of the line camera and adjustment of an aspect ratio.

Furthermore, according to a nineteenth aspect, in addition to the configuration explained above, in the image inspection program, the function of urging the user to adjust the pixel resolutions can further cause the computer to realize: a function of calculating pixel resolutions in a longitudinal direction and a lateral direction of the image captured by the line camera; and a function of adjusting an imaging parameter that specifies imaging conditions of the line camera.

Furthermore, an image inspection program according to a twentieth aspect is an image inspection program for performing a visual inspection of an inspection target object. The image inspection program causes a computer to realize: a function of setting an inspection target object for optical axis adjustment during inspection setting to a standstill state, irradiating illumination light on the inspection target object, repeatedly imaging, with a line camera in which a plurality of imaging elements are arrayed to be linearly arranged, the light reflected on the inspection target object, generating an image for optical axis adjustment having periodicity in a line direction of the line camera, and causing a display section to display the image for optical axis adjustment; a function of urging a user to adjust an optical axis of the line camera on the basis of the image for optical axis adjustment displayed on the display section; a function of setting a pattern for pixel resolution calculation having a known dimension as the inspection target object, repeatedly capturing images with the line camera while moving the pattern for pixel resolution calculation in one direction to generate an image for pixel resolution calculation; a function of receiving designation of a dimension measurement part on the image for pixel resolution calculation displayed on the display section; a function of measuring a dimension of the designated measurement part; a function of receiving an input of an actual dimension of the measurement part from the user and setting, as a pixel resolution calculation parameter, a ratio of the measured dimension and the input actual dimension; a function of adjusting an imaging interval of the line camera according to the set pixel resolution calculation parameter; and a function of repeating the imaging at the adjusted imaging interval to generate an image for inspection. With the configuration explained above, it is possible to easily perform troublesome setting work for imaging conditions of the line camera.

Furthermore, a computer-readable recording medium or a device having an image inspection program stored therein according to a twenty-first aspect is a computer-readable recording medium or a device having the image inspection program explained above stored therein. The recording medium includes magnetic disks, optical disks, magneto-optical disks, semiconductor memories, and other media capable of storing computer programs such as a CD-ROM, a CD-R, a CD-RW, a flexible disk, a magnetic tape, an MO, a DVD-ROM, a DVD-RAM, a DVD-R, a DVD+R, a DVD-RW, a DVD+RW, a Blu-ray (a commodity name) disk, and a HD DVD (AOD). The computer programs include, besides a computer program stored in the recording medium and distributed, a computer program distributed by download through a network line such as the Internet. Further, the device having the image inspection program stored therein includes a general-purpose or dedicated device in which the computer program is implemented in an executable state in a form of software, firmware, or the like. Furthermore, respective kinds of processing and functions included in the computer program may be executed by program software executable by a computer or processing of respective sections may be realized by hardware such as a predetermined gate array (FPGA or ASIC) or in a form in which the program software and a partial hardware module that realizes a part of elements of the hardware are mixed.

BRIEF DESCRIPTION OF THE DRAWINGS

FIG. 6A is an image diagram showing a phase of the raw image;

FIG. 6B is an image diagram showing a phase in which only a fluctuation component is extracted by taking a difference with respect to the phase shown in FIG. 6A;

FIG. 7A is an image diagram of an example of a depth contour image;

FIG. 7B is an image diagram of a specular albedo image obtained by imaging the same part as FIG. 7A;

FIG. 12A is an image diagram showing a photograph showing transparent work;

FIG. 12B is an image diagram showing a shape image of FIG. 12A;

FIG. 13A is an image diagram showing raw images of four phases obtained by imaging, from an X direction, a transparent film having gloss on the surface;

FIG. 13B is an image diagram showing raw images of four phases obtained by imaging the transparent film from a Y direction;

FIG. 15 is an image diagram showing a gloss ratio image obtained from FIGS. 14A and 14B;

FIG. 16A is an image diagram showing a phase X image showing a shift of a phase in the X direction obtained from FIG. 13A;

FIG. 16B is an image diagram showing a phase Y image showing a shift of a phase in the Y direction obtained from FIG. 13B;

DESCRIPTION OF EMBODIMENTS

Embodiments of the present invention are explained below with reference to the drawings. Note that the embodiments explained below are illustrations for embodying the technical idea of the present invention. The present invention is not limited to the embodiments. This specification does not limit members described in the claims to members described in the embodiments. In particular, dimensions, materials, shapes, relative arrangements, and the like of components described in the embodiments are not meant to limit the scope of the present invention to only the dimensions, the materials, the shapes, the relative arrangements, and the like unless specifically noted otherwise and are only explanation examples. Note that the sizes, positional relations, and the like shown by the drawings are sometimes exaggerated to clarify the explanation. Further, in the following explanation, the same names and the same signs indicate the same or homogeneous members. Detailed explanation of the members is omitted as appropriate. Further, as elements configuring the present invention, a plurality of elements may be configured by the same member and one member may share the plurality of elements. Conversely, a function of the one member can be allotted and realized by the plurality of members.

Image Inspection System 1000

Figure 1:
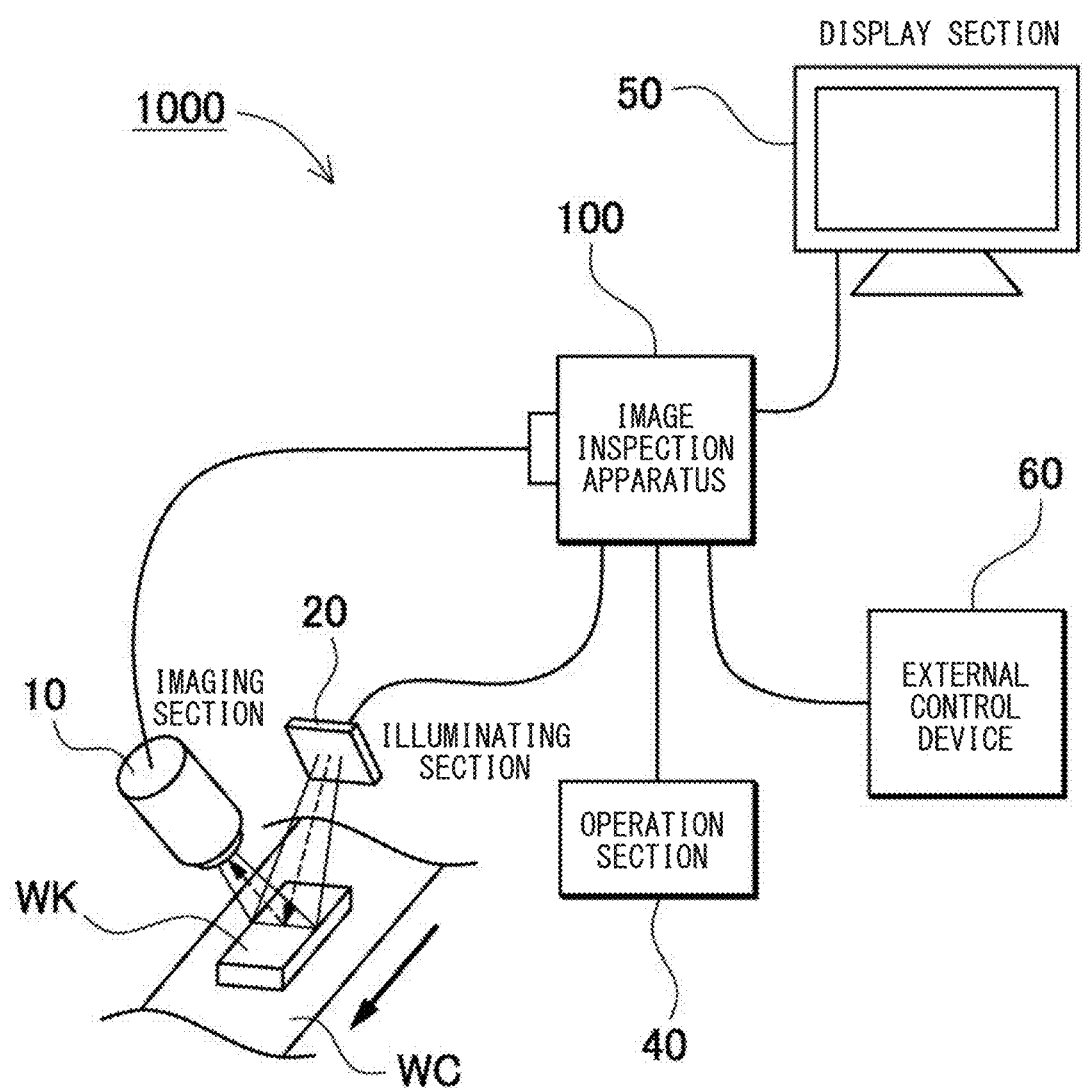
FIG. 1 is a block diagram showing an image inspection system according to a first embodiment of the present invention.

An image inspection system according to an embodiment of the present invention is shown in FIG. 1. An image inspection system 1000 shown in the figure includes an imaging section 10, an illuminating section 20, an image inspection apparatus 100, an operation section 40, a display section 50, and an external control device 60. The image inspection system 1000 acquires, with the imaging section 10 and the illuminating section 20, an image showing an exterior shape of an inspection target object or a subject (work WK), which is a target object on which a visual inspection is performed, executes an external inspection with the image inspection apparatus 100, outputs a result of the external inspection to the external control device 60 (e.g., a PLC), and causes the display section 50 to display the result according to necessity.

The work WK is conveyed on a work conveying mechanism WC. The image inspection system 1000 performs imaging on the moved work WK with the imaging section 10 and the illuminating section 20 to acquire information concerning a surface shape. The work conveying mechanism WC is a line of a conveyor controlled by a control device such as a programmable logic controller (PLC). Note that the imaging section 10 and the illuminating section 20 and the work only have to relatively move. For example, the work side may be fixed and the imaging section 10 side may be moved. Alternatively, both the sides can be moved.

The generation of an image may be performed on the imaging section 10 side or may be performed on the image inspection apparatus side. Further, the illuminating section 20 and the imaging section 10 are respectively set as separate members. Therefore, when the illuminating section 20 and the imaging section 10 are set, physical positioning of positions, angles, postures, and the like and adjustment work of a gain, shutter speed, an amount of light, and the like are necessary.

The image inspection apparatus 100 acquires an image, performs an image inspection according to necessity, and outputs an inspection result. Note that the image inspection is a product inspection executed using an image processing result of work. Examples of the image inspection include a non-defective product inspection for determining presence or absence of a flaw on the work surface and whether the work is non-defective as a product, a shape determination for determining appropriateness of an exterior shape, and reading (OCR) of a character string displayed on the surface of the work. The image inspection apparatus irradiates necessary illumination on the work to capture an image, performs image processing such as edge detection on obtained image data, and performs an image inspection such as pass/fail determination on the basis of a result of the image processing.

Operation Section 40

The operation section 40 is a member for performing various kinds of operation and setting on the image inspection apparatus 100. A keyboard, a console, a pointing device such as a mouse, or the like can be used.

Display Section 50

The display section 50 is a member for displaying an obtained image, a result of a visual inspection for the image, a setting screen for performing various kinds of setting, a setting value input to the setting screen from the operation section 40, and the like. The display section 50 is a display such as an LCD, a CRT, or an organic EL. When the display section 50 is a touch panel, the display section 50 can also be used as an operation section and a display section.

Image Inspection Apparatus 100

Figure 2A:
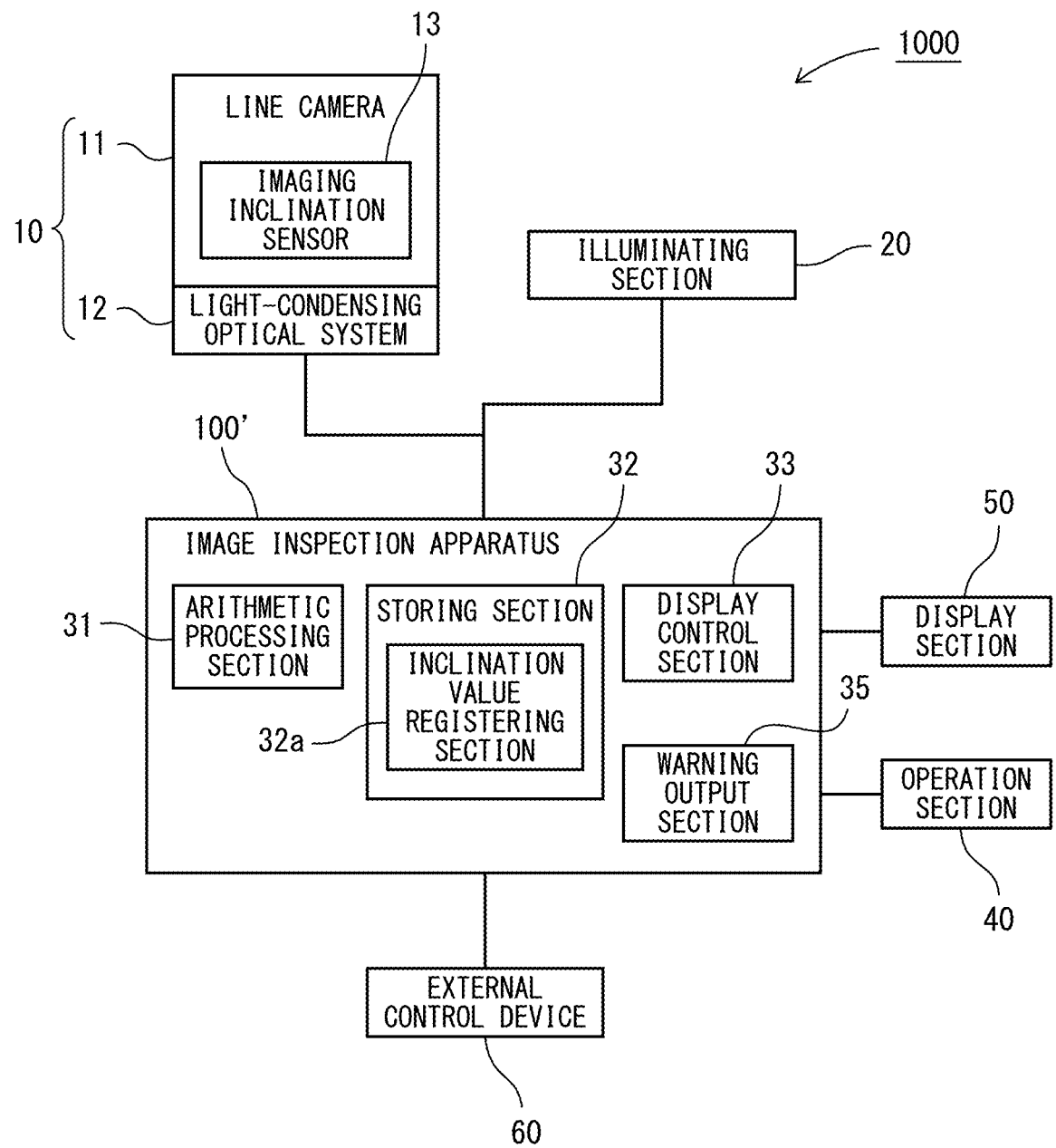
FIG. 2A is a block diagram showing an image inspection apparatus shown in FIG. 1.

An example of a functional block diagram of the image inspection system 1000 is shown in FIG. 2A. The image inspection system 1000 shown in the figure includes the imaging section 10, the illuminating section 20, and the image inspection apparatus 100. The operation section 40, the display section 50, and the external control device 60 are connected to the image inspection apparatus 100.

The image inspection apparatus 100 is a member for performing predetermined image processing on an image captured by the imaging section 10 and outputting a result of an image inspection. The image inspection apparatus 100 is configured by dedicated hardware. Besides, the image inspection apparatus 100 may be configured by installing software in a general-purpose apparatus, for example, installing an image inspection program in a general-purpose or dedicated computer. In an example of a configuration explained below, the image inspection program is installed in a dedicated computer in which hardware such as a graphic board is specialized for image inspection processing.

The imaging section 10 and the illuminating section 20 are selected according to a type of an image to be generated. For example, in the case of an optical image used for a desired inspection such as a flaw inspection or OCR, an area camera in which imaging elements are two-dimensionally arranged is used as the imaging section 10. A light source that irradiates illumination light on the work WK to be imaged is disposed in the illuminating section 20. Alternatively, when photographing of a stripe projection image necessary for height image generation in a photometric stereo method or triangulation is performed, a plurality of illuminations are disposed to irradiate illumination lights from opposed two or three directions. Alternatively, when a shape image of work is generated on the basis of the principle of phase measuring deflectometry (PMD; hereinafter referred to as "deflectometry"), a line camera disposed in a position where specular reflection light of the work is received is used as the imaging section 10.

The operations of the imaging section 10 and the illuminating section 20 are controlled by the image inspection apparatus 100. The image inspection apparatus 100 synchronizes timing of projection of illumination light by the illuminating section 20 and timing of imaging by the imaging section 10. In the following explanation, in this specification, an example is explained in which a shape image is generated by the deflectometry (details are explained below).

Figure 3:
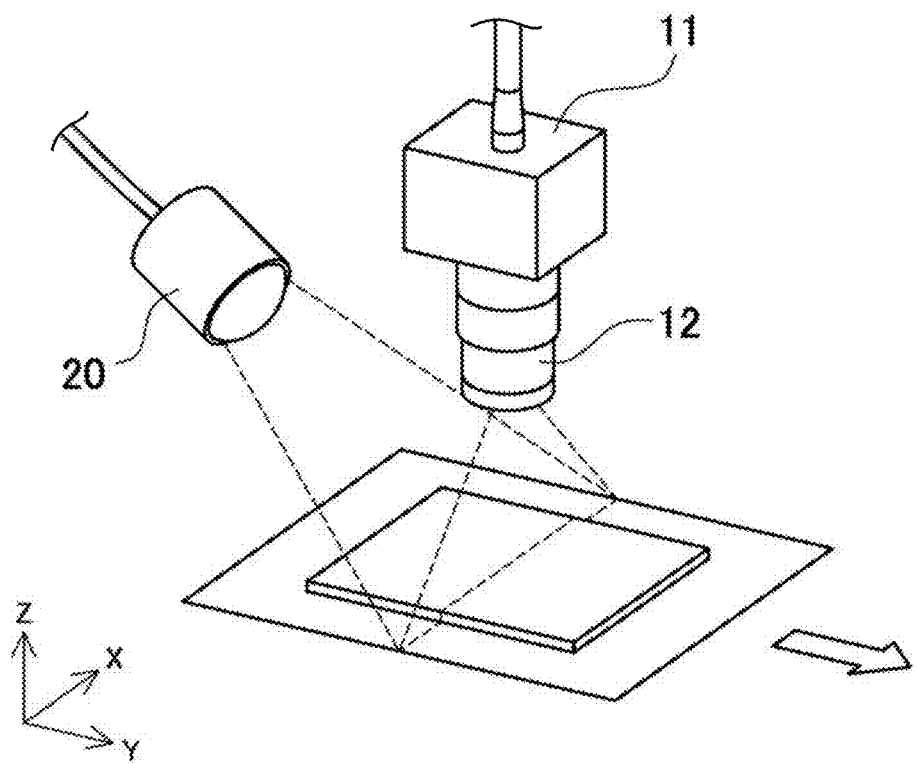
FIG. 3 is a perspective view showing a state in which work is imaged by an imaging section.

The imaging section 10 includes, as shown in FIG. 3, a line camera 11 and a light-condensing optical system 12. The imaging section 10 includes an imaging inclination sensor 13. The imaging inclination sensor 13 is a sensor for detecting an inclination angle of the imaging section 10. A gravitational acceleration sensor can be suitably used as the imaging inclination sensor 13. The imaging inclination sensor 13 is desirably incorporated in the imaging section 10. However, the imaging inclination sensor 13 may be a separate member or may be externally attached to the imaging section 10 rather than being integrated with the imaging section 10.

The light-condensing optical system 12 is an optical system for condensing reflected light of the illumination irradiated on the work WK from the illuminating section 20 and reflected on the work WK. Typically, the light-condensing optical system 12 is one or more optical lenses.

The line camera 11 is a camera in which a plurality of imaging elements are arrayed to be linearly arranged. The line camera 11 is a member for receiving the reflected light condensed by the light-condensing optical system 12. Imaging elements such as CCDs or C-MOSs linearly arranged can be used.

The illuminating section 20 is a member for irradiating illumination light on the work WK. The illuminating section 20 includes a light source. As the light source, a light emitting diode (LED), liquid crystal (LCD), an organic EL, a halogen lamp, and the like can be used. In particular, an illuminating section in which a plurality of LED elements are arranged is desirable because the illuminating section has a large amount of light and high directivity.

As shown in FIG. 3, with respect to the optical axis of the light-condensing optical system 12, a direction parallel to the optical axis is represented as a Z axis, a direction orthogonal to the Z axis and parallel to an arranging direction of the imaging elements is represented as an X axis, and a direction orthogonal to the X axis and the Z axis is represented as a Y axis. In FIG. 3, work is conveyed in the X direction.

Imaging Inclination Sensor 13

The imaging inclination sensor 13 outputs values indicating inclinations of the X axis, the Y axis, and the Z axis of the imaging section 10 with respect to the horizontal direction or the gravity direction.

The image inspection apparatus 100 performs communication with the imaging section 10, acquires a value indicating gravitational acceleration from the imaging inclination sensor 13, and causes the display section 50 to display the value. The image inspection apparatus 100 includes an arithmetic processing section 31, a storing section 32, a display control section 33, and a warning output section 35.

Arithmetic Processing Section 31

The arithmetic processing section 31 is a member for performing various kinds of processing such as an image inspection. The arithmetic processing section 31 converts a value output by the imaging inclination sensor 13 into a numerical value easily understandable for a user when the arithmetic processing section 31 causes the display section 50 to display the value. Further, during optical axis adjustment, the arithmetic processing section 31 also functions as an image-for-optical-axis-adjustment generating section that repeatedly images, with the line camera 11, work for optical axis adjustment in a standstill state and generates images for optical axis adjustment having periodicity in a line direction of the line camera 11.

Figure 27:
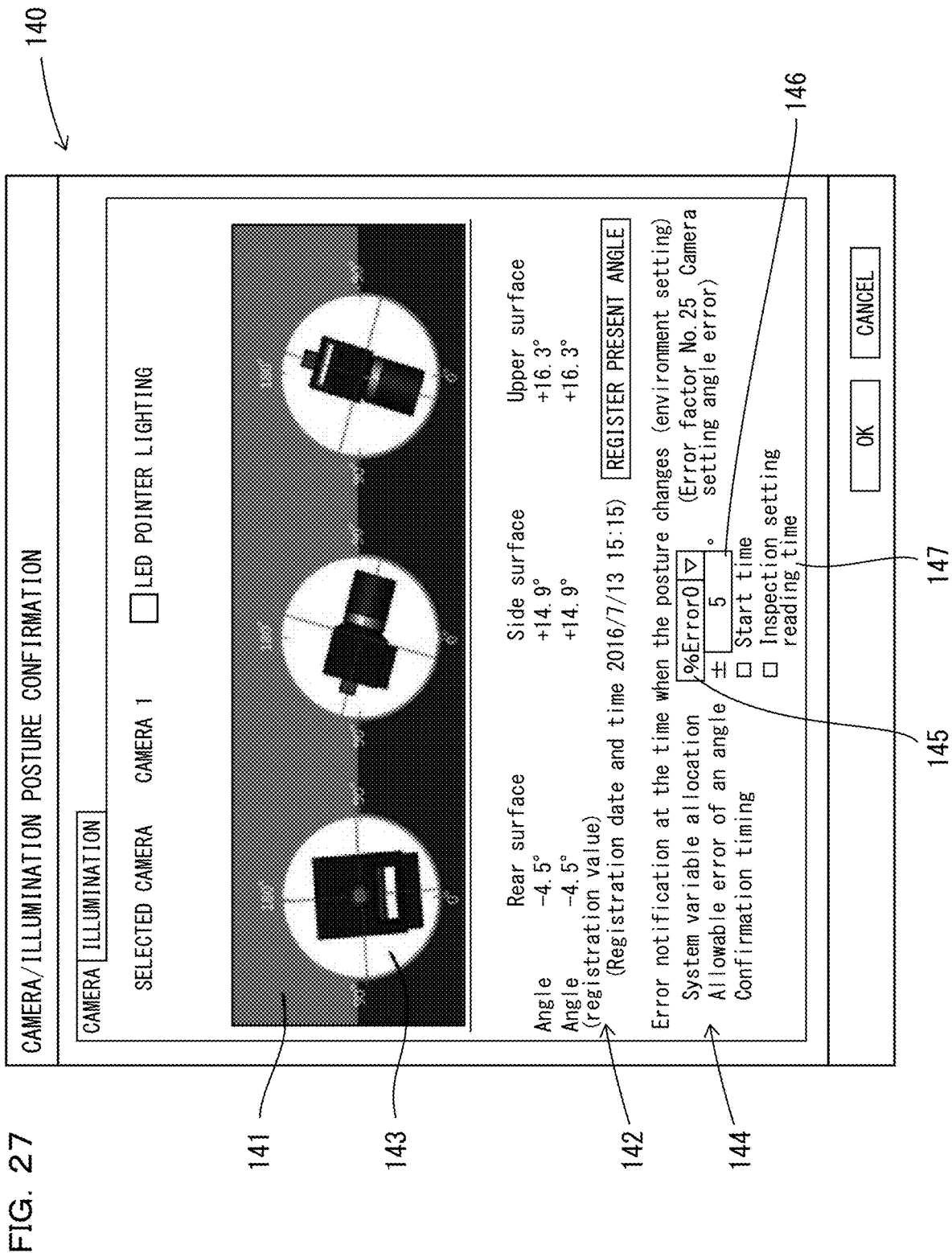
FIG. 27 is an image diagram showing a camera posture display screen of the image inspection program.

The storing section 32 is a member for saving various image data and setting data. The storing section 32 retains a value output by the imaging inclination sensor 13 in order to store a posture of the imaging section 10 at a certain point in time. The storing section 32 functions as an inclination value registering section 32a that registers a value indicating inclination of an imaging schematic view 143 (explained below; FIG. 27, etc.) representing an inclination state of the imaging section 10. As the storing section 32, a nonvolatile memory such as a semiconductor memory and hard disk can be used. Alternatively, the storing section 32 may be a recording medium. As a media reading section, that is, as a member for reading or writing in a portable medium, a standardized recording medium such as a USB memory (a commodity name) or an SD card (a commodity name), a semiconductor memory, or the like can be connected to the storing section 32 to enable reading and writing of data. The storing section 32 may be configured to perform exchange of data between the storing section 32 and an external recording device through wireless connection or network connection.

The display control section 33 is a member for controlling display content of the display section 50. For example, the display control section 33 controls the display content of the display section 50 to incline or rotate and display the imaging schematic view 143 (explained below; FIG. 27, etc.) according to the posture of the imaging section 10. Specifically, the display control section 33 causes, on the basis of the value indicating the inclination output from the imaging inclination sensor 13, the display section 50 to display values indicating figures or inclinations indicating degrees of at least any two inclinations among inclinations of the X axis, the Y axis, and the Z axis of the imaging section 10. The display control section 33 can also cause the display section 50 to display a value indicating present inclination together with values of inclinations in the past stored in the storing section 32.

Warning Output Section 35

The warning output section 35 performs a comparison operation to determine whether a value indicating present inclination is within a range of an allowable error with respect to the values indicating the inclinations in the past stored in the storing section 32 and, if the value exceeds the allowable error, outputs a warning. Examples of the output of the warning include a form for sending a warning signal to the external control device 60 and a form for displaying a warning message on the display section 50. In response to the warning, predetermined operation, for example, operation for sounding a buzzer of warning or displaying a warning message or emitting a maintenance call in order to urge the user to maintain the system is executed. Consequently, it is possible to take measures for, for example, warning and informing the user that the posture of the imaging section 10 changes because of aged deterioration, a shock, vibration, or the like and it is likely that a correct image inspection is not performed or automatically performing necessary processing.

For example, during setting of the image inspection apparatus 100, at least any one inclination value among inclination values of the X axis, the Y axis, and the Z axis output from the imaging inclination sensor 13 is registered in the inclination value registering section 32a as a registration value. During actual operation of the image inspection apparatus 100, the warning output section 35 determines whether an inclination value output from the imaging inclination sensor 13 does not deviate from a registration value registered in the past by the inclination value registering section 32a by more than a threshold decided in advance as an allowable error. As a result of the determination, when the inclination value deviates from the registration value by more than the threshold, the warning output section 35 outputs a warning.

As timing for the comparison with the threshold by the warning output section 35, the warning output section 35 can always perform the comparison at a predetermined interval, for example, an interval of 10 ms or can perform the comparison in each event such as a start time, a shutdown time, or a maintenance time of the image inspection apparatus 100.

The members configuring the image inspection apparatus 100, for example, the arithmetic processing section 31, the display control section 33, and the warning output section 35 can be configured by ASICs or the like.

Display Section 50

The display section 50 can be included in the image inspection apparatus 100. The display section 50 is connected to the display control section 33. The display section 50 displays various kinds of setting, the imaged work WK, a direction of the work WK, and the like. The display section 50 is capable of updating and displaying degrees of at least any two inclinations on a real-time basis. Consequently, during setting of the imaging section 10, it is possible to cause the display section 50 to display present inclination on a real-time basis. As a result, the user can easily adjust inclination of the imaging section 10 on the basis of the inclination.

The display section 50 can display, on the basis of the value indicating the inclination output from the imaging inclination sensor 13, figures or values indicating degrees of at least any two inclinations among the inclinations of the X axis, the Y axis, and the Z axis of the imaging section 10. Consequently, during the setting of the imaging section 10, it is possible to cause the display section 50 to display the present inclination. The user can easily adjust the inclination of the imaging section 10 on the basis of the inclination.

Imaging Schematic View 143

Further, as shown in FIG. 27 and the like referred to below, the display section 50 can display, in a predetermined reference posture, the imaging schematic view 143 simulating the exterior of the imaging section 10 and display, over the imaging schematic view 143, an inclination axis inclined by an angle corresponding to at least any two inclinations. Consequently, the user can visually grasp inclination of the imaging section 10. The display section 50 may display, over the imaging schematic view 143, a vertical line extending along the gravity direction and display, over the imaging schematic view 143, an inclination axis inclined by an angle corresponding to at least any two inclinations. Further, the display section 50 can also display the imaging schematic view 143 respectively as plan views displayed on a YZ plane (the X axis), an XZ plane (the Y axis), and an XY plane (the Z axis). Alternatively, the imaging schematic view 143 is not limited to a plane display form and can be stereoscopically displayed as a perspective view or the like.

Identification Display Function for an Unstable Surface

Among surfaces configuring the imaging schematic view 143, an unstable surface can be displayed to be distinguished from other parts. The unstable surface indicates a surface in which an output of inclination is unstable because the gravitational acceleration sensor has two axes (an angle in a direction that cannot be detected by the two axes). As a form of identification display for distinguishing the unstable surface from the other surfaces, for example, the unstable surface can be displayed at transmittance higher than the transmittance of the other parts or can be hidden. Further, the display section 50 can simultaneously display an inclination value registered in the inclination value registering section 32a and a present inclination value of the imaging section 10 output by the imaging inclination sensor 13. By performing the identification display that can distinguish a certain unstable surface from the other surfaces, the user can appropriately grasp a surface that the user should be aware and a surface that the user should not be aware. Details of the above are explained below.

The warning output section 35 is not limited to a configuration in which targets of warning output are all of the three axes of the X axis, the Y axis, and the Z axis and may be configured to emit a warning for only any axis. For example, an axis set as a target of warning output by the warning output section 35 can be selected out of the X axis, the Y axis, and the Z axis. Consequently, whereas an output is unstable in an axis having weak gravity action, it is possible to exclude the axis from the target of warning output to avoid an unnecessary warning.

Further, the warning output section 35 can be configured to be capable of individually setting a threshold for an inclination value of the selected axis set as the target of warning output. Consequently, it is possible to exclude, for example, an axis having an unstable output and weak gravity action from the target of warning output. Consequently, it is possible to perform flexible setting to, for example, set a threshold rather loose for an unstable axis.

Illuminating Section 20

As shown in FIG. 3, a direction parallel to an optical axis of illumination light (an illumination optical axis) is represented as a Z axis, a direction orthogonal to the Z axis and parallel to an array direction of illuminating elements is represented as an X axis, and a direction orthogonal to the X axis and the Z axis is represented as a Y axis. Note that the array direction of the illuminating elements is not limited to only one direction. The illuminating elements may be arranged in the X-axis direction and the Y-axis direction. For example, an LCD panel, an organic EL panel, or the like may be used as an illumination.

In the image inspection apparatus 100, an inclination sensor can be provided not only on the imaging section 10 side but also on the illuminating section 20 side. Such an example is shown in a functional block diagram of FIG. 2B as an image inspection apparatus 100' according to a modification. An illumination inclination sensor 23 on the illuminating section 20 side is capable of outputting values indicating inclinations of the X axis, the Y axis, and the Z axis of the illuminating section 20 with respect to the horizontal direction or the gravity direction.

Figure 28:
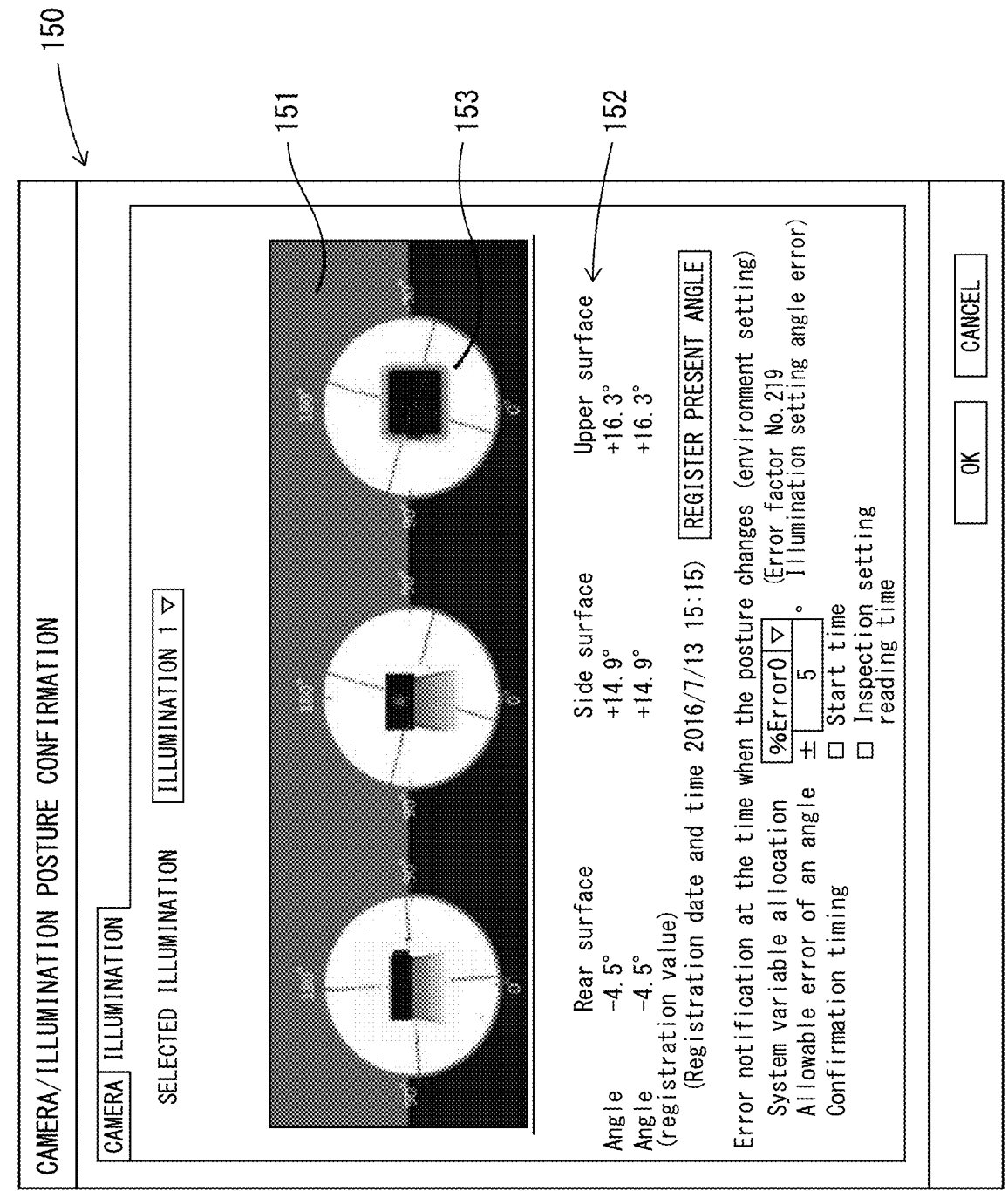
FIG. 28 is an image diagram showing an illumination posture display screen of the image inspection program.

As shown in FIG. 28 and the like referred to below, an illumination schematic view 153 simulating the illuminating section 20 indicating degrees of inclinations of the X axis, the Y axis, and the Z axis can be displayed on the display section 50. Consequently, the user can visually distinguish a light emitting surface of the illuminating section 20 from the display section 50. As in the imaging schematic view 143 explained above, the light emitting surface that emits illumination light among surfaces configuring the illumination schematic view 153 can be displayed to be distinguished from the other surfaces.

Figure 2B:
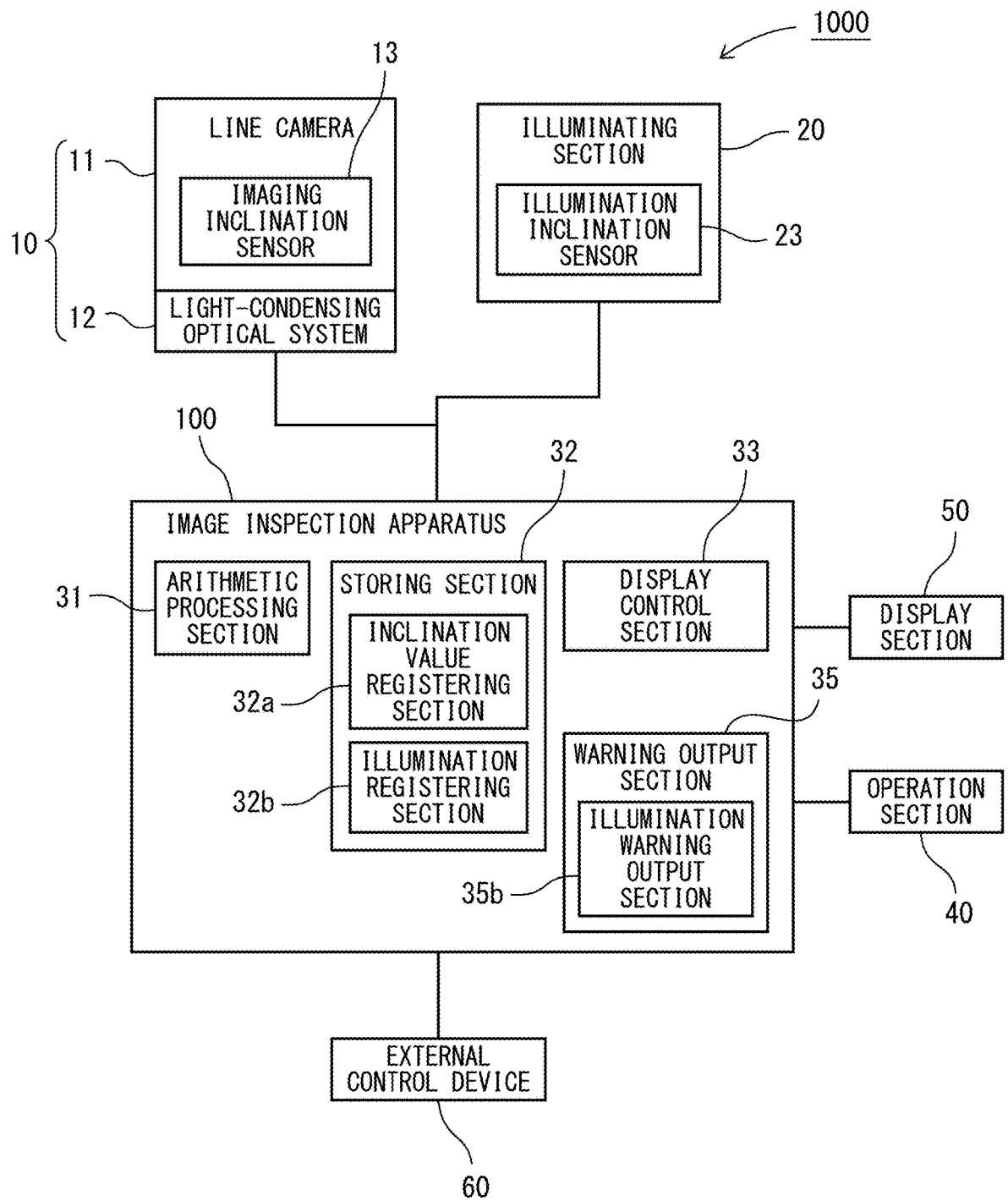
FIG. 2B is a block diagram showing an image inspection apparatus according to a modification.

In the image inspection apparatus 100' shown in FIG. 2B, the same members as the members of the image inspection apparatus 100 shown in FIG. 2A are denoted by the same reference numerals and signs. Detailed explanation of the members is omitted. The illuminating section 20 includes an illumination inclination sensor 23b. The storing section 32 functions as, in addition to the inclination value registering section 32a of the imaging section 10, an illumination registering section 32b that registers an illumination inclination value of the illuminating section 20. Further, in addition to the warning function of the imaging section 10, the warning output section 35 functions as an illumination warning output section 35b that outputs a warning when an inclination value output from the illumination inclination sensor 23b deviates from a registration value registered last by the illumination registering section 32b by more than a threshold decided in advance at the time of operating the image inspection apparatus 100.

The image inspection apparatus 100' performs communication with the imaging section 10 and the illuminating section 20, acquires values indicating gravitational acceleration respectively from the imaging inclination sensor 13 and the illumination inclination sensor 23, and causes the display section 50 to display the values. The arithmetic processing section 31 converts values output by the imaging inclination sensor 13 and the illumination inclination sensor 23 into numerical values easily understandable for the user when the arithmetic processing section 31 causes the display section 50 to display the values. The display control section 33 controls display content of the display section 50 to incline or rotate to display the imaging schematic view 143 according to the posture of the illuminating section 20 in addition to the posture of the imaging section 10. The storing section 32 registers a value indicating inclination of the imaging schematic view 143 in the inclination value registering section 32a and registers inclination of the illumination schematic view 153 representing an inclination state of the illuminating section 20 in the illumination registering section 32b. The illumination warning output section 35b compares the registered inclination values of the imaging section 10 and the illuminating section 20 respectively with individually set thresholds and, when determining that the inclination values are outside ranges of the thresholds, emits a warning output. As in the case of the imaging section 10, the illumination warning output section 35b may be capable of selecting a target of the illumination warning output out of the X axis, the Y axis, and the Z axis.

Figure 2C:
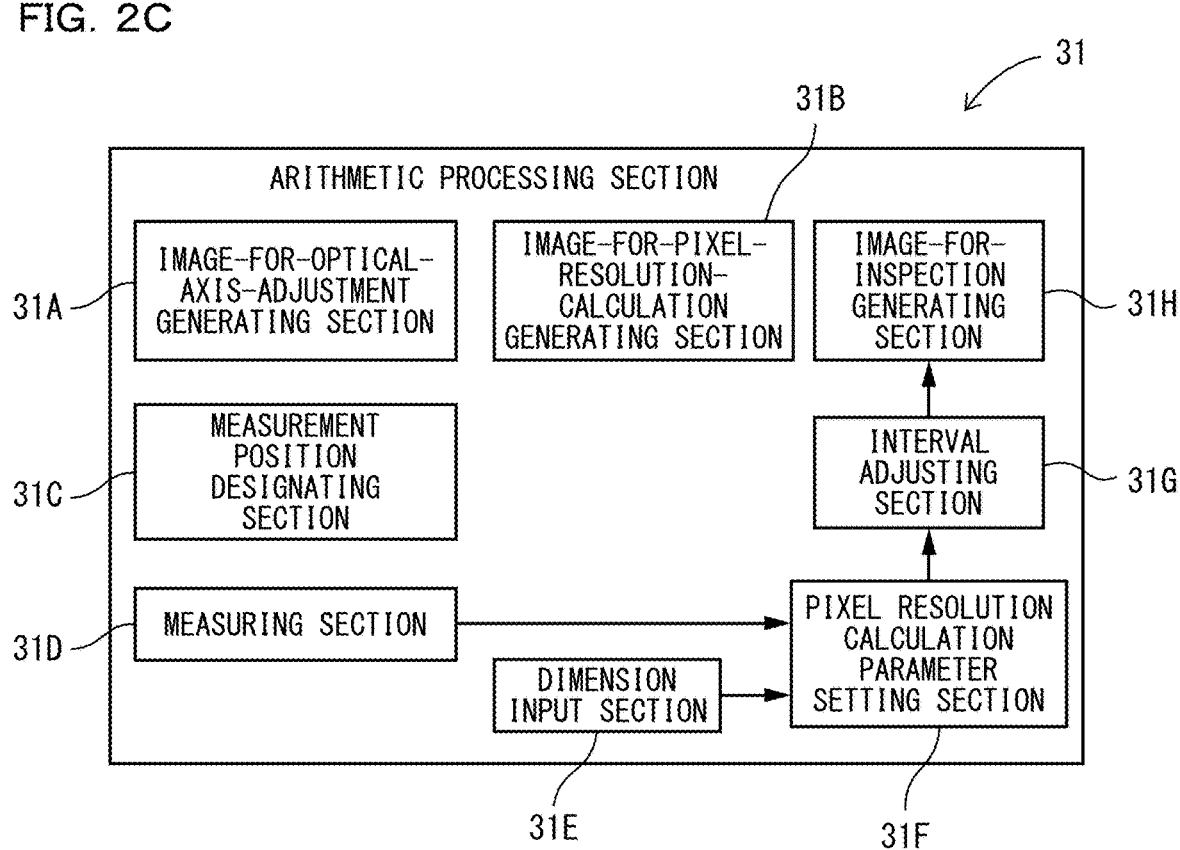
FIG. 2C is a block diagram showing an example of an arithmetic processing section.

An example of a functional block diagram of the arithmetic processing section 31 is shown in FIG. 2C. The arithmetic processing section 31 shown in the figure includes an image-for-optical-axis-adjustment generating section 31A, an image-for-pixel-resolution-calculation generating section 31B, a measurement position designating section 31C, a measuring section 31D, a dimension input section 31E, a pixel resolution calculation parameter setting section 31F, an interval adjusting section 31G, and an image-for-inspection generating section 31H.

The image-for-optical-axis-adjustment generating section 31A is a member for, during inspection setting, repeatedly capturing images of an inspection target object for optical axis adjustment in a standstill state with the line camera 11 to generate an image for optical axis adjustment having periodicity in the line direction.

The image-for-pixel-resolution-calculation generating section 31B is a member for, after optical axis adjustment of the line camera 11 is performed on the basis of the image for optical axis adjustment generated by the image-for-optical-axis-adjustment generating section 31A and displayed on the display section 50, repeatedly capturing images with the line camera 11 while moving a pattern for pixel resolution calculation having a known dimension in one direction to generate an image for pixel resolution calculation.

The measurement position designating section 31C is a member for receiving designation of a dimension measurement part on the image for pixel resolution calculation displayed on the display section 50.

The measuring section 31D is a member for measuring a dimension of the measurement part designated by the measurement position designating section 31C.

The dimension input section 31E is a member for receiving an input of an actual dimension of the measurement part from the user.

The pixel resolution calculation parameter setting section 31F is a member for setting, as a pixel resolution calculation parameter, a ratio of the dimension measured by the measuring section 31D and the actual dimension input to the dimension input section 31E.

The interval adjusting section 31G is a member for adjusting an imaging interval of the line camera 11 according to the pixel resolution calculation parameter set by the pixel resolution calculation parameter setting section 31F.

The image-for-inspection generating section 31H is a member for repeating imaging at the imaging interval adjusted by the interval adjusting section 31G and generating an image for inspection (details are explained below).
Deflectometry As a method with which the imaging section 10 acquires a shape of the work WK, various methods can be used. Examples of the method include deflectometry, a phase shift method, a stereo method, a lens focus method, a light sectioning method, an optical radar method, an interference method, and a TOF method. In the following explanation, in this embodiment, as an example of a configuration in which a shape image of work is generated making use of the deflectometry principle, a configuration in which a shape image of work is acquired from a phase map calculated on the basis of the deflectometry principle is explained with reference to FIG. 3 and the like.

In the deflectometry, the imaging section 10 is disposed in a position where specular reflection light of the work WK is received. In this example, only one line is imaged by one imaging using the line camera 11 as the imaging section 10. As shown in FIG. 3, a line for imaging the work WK with the imaging section 10 is relatively changed (in the Y direction) by moving the work WK side (or the imaging section 10 side). A two-dimensional image is configured by imaging a plurality of lines. In an example shown in FIG. 3, the imaging section 10 is fixed and the work WK side is placed on the movable work conveying mechanism WC and moved.

In the deflectometry processing, the processing can be performed for each of pixels. Therefore, a frame memory and a line memory are unnecessary. This is advantageous in terms of simplification of a configuration and a cost reduction. On the other hand, an image captured by the line camera is linear. Therefore, it is difficult to confirm what kind of image is obtained and whether setting of the line camera and the illuminating section is correct. In general, in a measurement system that measures a shape of work, positioning work is necessary in setting of a camera section and an illuminating section. On the other hand, in particular, in the deflectometry processing, a normal two-dimensional image is not obtained by simply performing imaging. Therefore, it is extremely useful to provide a function of assisting the setting of the line camera and the illuminating section.

A procedure of imaging is explained with reference to a flowchart of FIG. 4. First, the image inspection apparatus performs imaging in step S401. An illumination pattern of illumination light irradiated from the illuminating section is projected eight times in total to acquire one line of a post-processing image. In other words, the imaging is performed eight times (for eight lines) in order to generate an image for one line. In FIG. 5, an example of a raw image obtained by the eight times of the imaging is shown as an intermediate image. In FIG. 5, the longitudinal direction is a flowing direction of work (the Y direction). Therefore, one pixel is arranged in the longitudinal direction. The illumination pattern is changed four times in the X direction for each one pixel to perform imaging. Further, the illumination pattern is changed four times in the Y direction to perform imaging. Note that a part equivalent to one line is imaged eight times in a state in which the work is moving on a stage. Therefore, strictly, respective lines are imaged while being shifted by ⅛ line.

Subsequently, in step S402, the image inspection apparatus performs the deflectometry processing. The raw image is divided into a diffuse component (a diffuse albedo image), a specular reflection component (a specular albedo image), and phases (two phases in the X direction and the Y direction) by the deflectometry processing. Note that the components are processed in 8 bits.

In step S403-1 and step S403-2, the image inspection apparatus performs contrast corrections respectively on the diffuse component and the specular reflection component. The contrast corrections are linear corrections. For example, an average of an ROI is corrected to be a median. In the case of 8 bits ($2^8$=256), a 128 level is set as the median. Consequently, a diffuse component after the correction and a reflection component after the correction are obtained.

On the other hand, concerning the phase components, the image inspection apparatus takes a difference from a reference phase in step S403-3. A difference is acquired with respect to a phase of a reference plane. For example, the user designates a spherical shape, a cylindrical shape, a plane shape, and the like as the reference plane. Differences from the spherical shape, the cylindrical shape, the plane shape, and the like are acquired. Alternatively, a difference may be extracted on a free curved surface. For example, when a difference is taken with respect to a phase of a raw image shown in FIG. 6A, a phase in which only a fluctuation component is extracted appears as shown in FIG. 6B. In this way, phases after the correction (differences; two phases in the X direction and the Y direction) are obtained.

Further, in step S404-1, step S404-2, and step S404-3, the image inspection apparatus performs hierarchization respectively on the diffuse component, the specular reflection component, and the phases (the differences) after the correction. As the hierarchization, ½ reduction is respectively repeated for the images. Consequently, a hierarchical diffuse albedo image, a hierarchical specular albedo image, and hierarchical phase images (two hierarchical phase images in the X direction and the Y direction) are obtained. The phases have accuracy of, for example, 16 bits.

Depth Contour Image

The phases (the differences) are not only directly hierarchized. In step S404-4, the image inspection apparatus obtains a depth contour image for the phases (the differences). The depth contour image is an intermediate image in which a portion having a large phase difference is emphasized. The depth contour image is a concept different from a curvature. The depth contour image has advantages that, for example, the depth contour image is considerably higher in speed than the shape image, a line flaw is extremely easily seen, and it is easy to extract a contour. On the other hand, the depth contour image has characteristics that a specific shape, for example, a thin wide dent is less easily extracted, distinction of unevenness is difficult, and the depth contour image can be used only on a flat surface. An example of the depth contour image is shown in FIG. 7A. For reference, a specular albedo image obtained by imaging the same part is shown in FIG. 7B.

Further, in step S405-2, the image inspection apparatus performs hierarchization for the depth contour image as well to obtain a hierarchical depth contour image.

Shape Stacking

Figure 8:
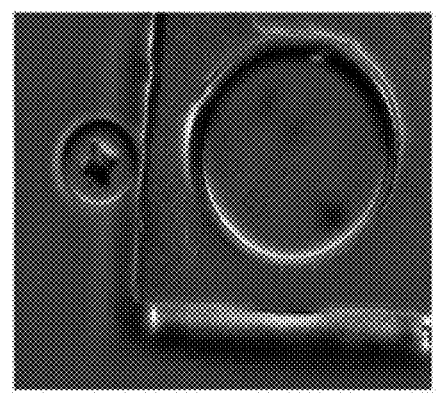
FIG. 8 is an image diagram showing an example of a shape image.

On the other hand, in step S405-1, the image inspection apparatus performs shape stacking on the hierarchical phase image to generate a shape image. An example of the shape image obtained in this way is shown in FIG. 8. A method of forming the shape image is basically a method similar to the photometric stereo method. Processing such as wrapping of a phase is different. As weight information, a specular albedo image shown in FIG. 7B can also be used. The method of the shape stacking is effective for a large area defect (e.g., a thin wide dent). Distinction of unevenness is easy. On the other hand, the method of the shape stacking is disadvantageous in that a plane is distorted in a round shape, a thin line flaw less easily appears, and, in the case of an edge, height is inaccurate and ringing occurs.

In step S406, the image inspection apparatus performs simple defect extraction to acquire a defect image. The simple defect extraction is a function of easily extracting a defect from the shape image. Note that it is not essential to use the simple defect extraction. The specular reflection component image and the diffuse component image can also be used as an input image.

Details of the Deflectometry Processing

Figure 4:
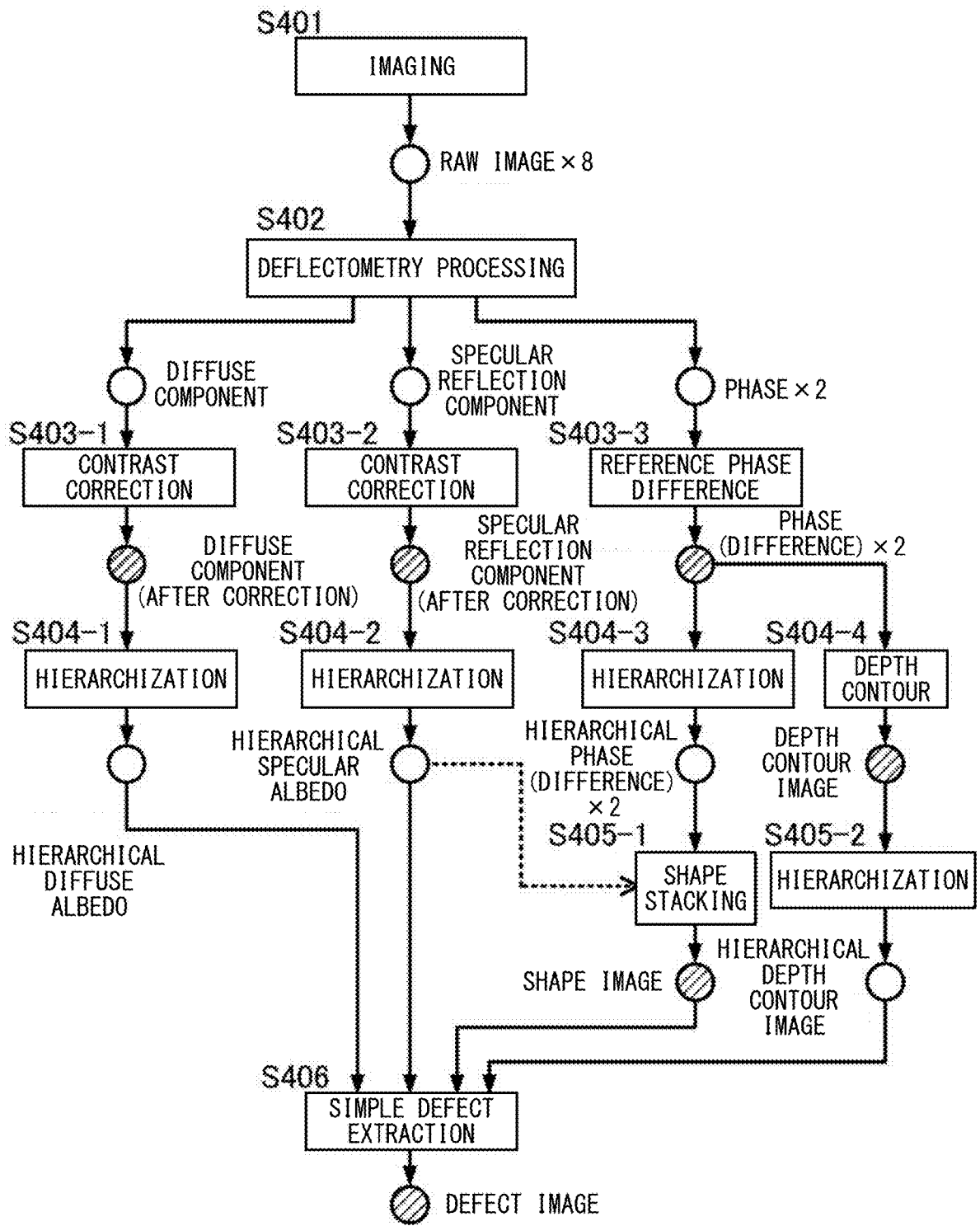
FIG. 4 is a flowchart for explaining a procedure for acquiring a shape image of the work on the basis of the deflectometry principle.
Figure 5:
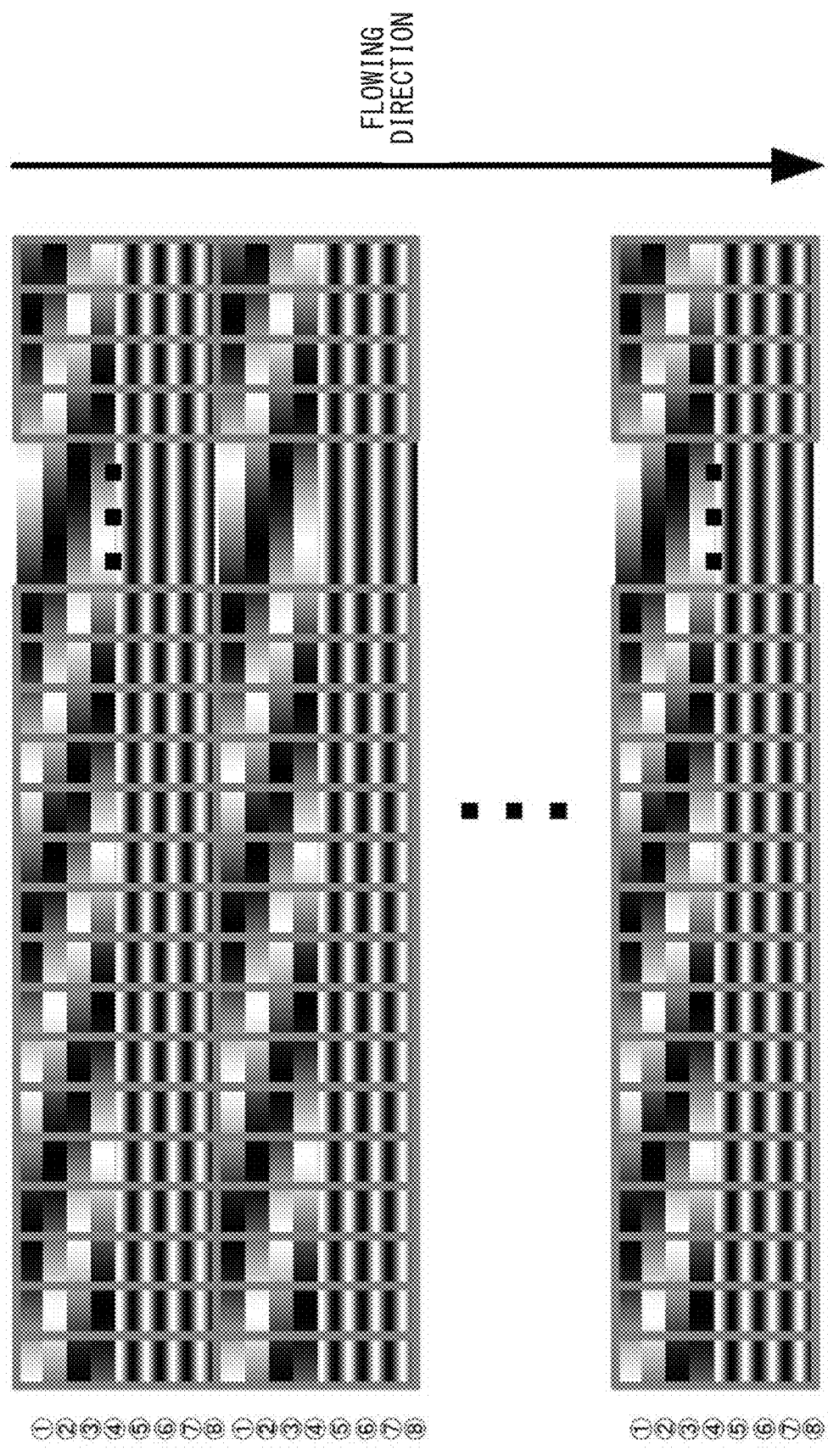
FIG. 5 is an image diagram showing a raw image obtained by eight times of imaging.
Figure 9:
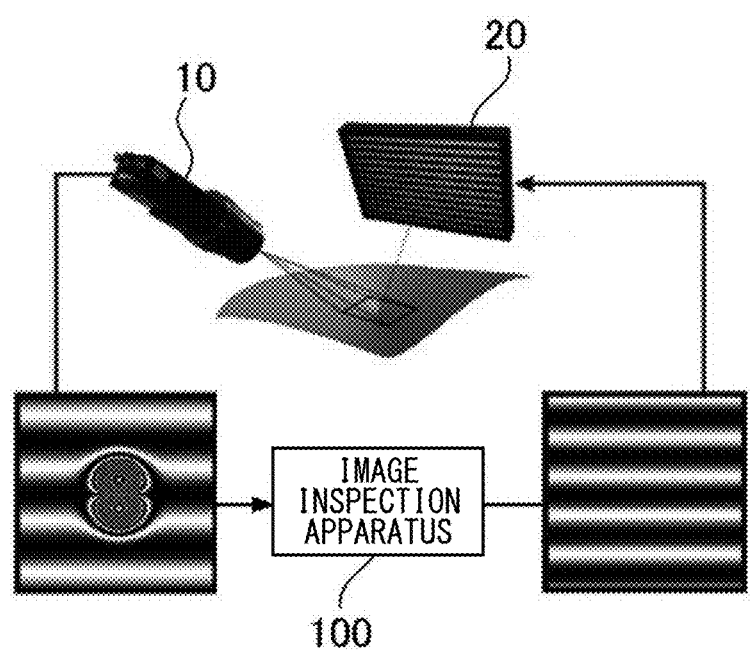
FIG. 9 is a schematic diagram showing a configuration in which a shape image of work is acquired on the basis of the deflectometry principle.

Details of the deflectometry processing performed in step S402 in FIG. 4 explained above are explained. It is assumed that stripe illumination is projected from the illuminating section 20 and distortion of the stripe illumination is photographed using the imaging section 10 and the illuminating section 20 shown in FIG. 9. States of the stripe illumination and specular reflection and diffuse reflection obtained by reflection on a work surface are shown in FIG. 10.

Figure 10:
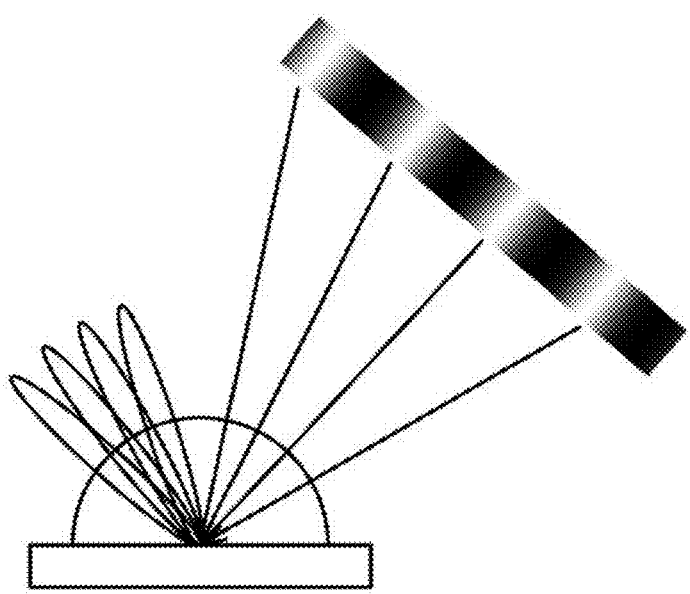
FIG. 10 is a schematic diagram showing states of stripe illumination and specular reflection and diffuse reflection obtained by reflection on a work surface.

As shown in FIG. 10, a stripe illumination section reflects a projection pattern of a stripe on the surface of work while shifting a phase. In this state, the intensity of the reflection of the stripe is calculated. Consequently, a specular reflection component is obtained. The specular reflection component has a shift from the intensity of a phase of the stripe. Angle resolution is obtained by dividing an angle by gradation from an angle/cycle ratio.

On the other hand, a surface gradient is obtained by calculating a shift of the phase of the stripe. Further the intensity of the diffuse reflection is also acquired.

Reflected Image

A reflected image, that is, an original image is given by the following expression. Four patterns of images in which reflection of the stripe and a diffuse component (including an environment component) are mixed are captured.

$$I_1 = R_d + R_s \sin(\varphi_s)$$
$$I_2 = R_d + R_s \sin\left(\varphi_s + \frac{\pi}{2}\right)$$
$$I_3 = R_d + R_s \sin(\varphi_s + \pi)$$
$$I_4 = R_d + R_s \sin\left(\varphi_s + \frac{3\pi}{2}\right)$$

Specular Reflection Component

The specular reflection component is given by the following expression. A diffuse component is excluded by a difference between reverse phases.

$$R_s = \frac{\sqrt{(I_3 - I_1)^2 + (I_4 - I_2)^2}}{2}$$

Specular Reflection Angle

The specular reflection angle (phase) is given by the following expression. An angle is calculated as tan θ=sin θ/cos θ by a π/2-shifted specular reflection component.

$$\varphi_s = \tan^{-1} \frac{I_2 - I_4}{I_3 - I_1}$$

Average Image

The average image is given by the following expression. The average image includes a diffuse component and an environment component. A specular reflection component is excluded by addition of reverse phases.

$$\bar{I} = \frac{\sum_{i=1}^{4} I_i}{4}$$

Diffuse Reflection Image

The diffuse reflection image is given by the following expression.

$$R_d = \bar{I} - \frac{R_s}{2}$$

Among the images explained above, the specular reflection component, the specular reflection angle, the average image, and the diffuse reflection images are images to be output. Processing of the images are performed respectively on an X-direction stripe and a Y-direction stripe.

Further, a shape image can be obtained by further performing stacking calculation by a Gauss-Jacobi method or the like on specular reflection angles (phase images) in the X direction and the Y direction.

In general, in many examples, a shape is restored by the triangulation or the like after unwrapping is performed. On the other hand, in this embodiment, the unwrapping is avoided. A shape is restored without depending on the triangulation by performing stacked calculation of a local differential value with the Gauss-Jacobi method. As a shape restoration method, a known method can be used as appropriate. Desirably, the triangulation is not used. The shape restoration method is a hierarchical method having reduced images in multiple stages. Note that the shape restoration method can also be a method having a difference between a reduced image and a normal image.

Further, a characteristic size can also be set as a parameter. The characteristic size is a parameter for setting size of a flaw of a detection target corresponding to a purpose and a type of an inspection. For example, the characteristic size is set such that a finest flaw can be detected when a parameter value of the characteristic size is 1 and a larger flaw can be detected as the value is increased. Consequently, when the characteristic size is increased, a larger flaw can be easily detected. Unevenness on the work surface is made clear.

Image of Deflectometry

Figure 11A:
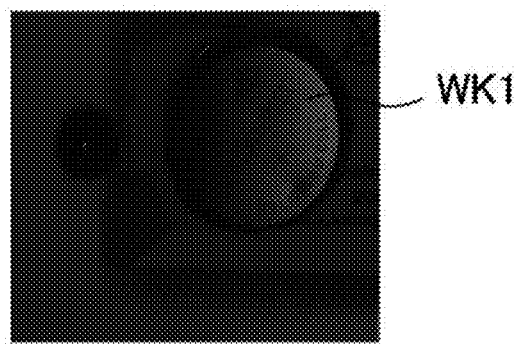
FIG. 11A is an image diagram showing an original image of the work.
Figure 11B:
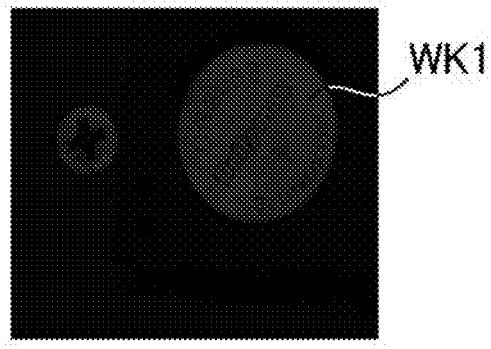
FIG. 11B is an image diagram showing a specular reflection component.
Figure 11C:
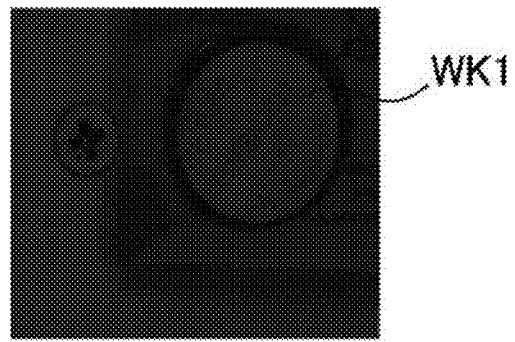
FIG. 11C is an image diagram showing a diffuse reflection component.
Figure 11D:
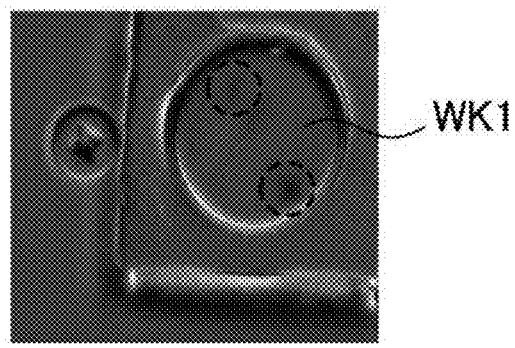
FIG. 11D is an image diagram showing a shape image.

Examples of images obtained by such deflectometry processing are shown in FIGS. 11A to 11D. In these figures, FIG. 11A shows an original image, FIG. 11B shows a specular reflection component, FIG. 11C is a diffuse reflection component, and FIG. 11D shows a shape image. As shown in FIG. 11D, it can be confirmed that a shape image in which an unevenness state of work is easily grasped is obtained. Note that, in the examples shown in FIGS. 11A to 11D, a button battery is imaged as work WK1. However, the work is not limited to such opaque work. For example, unevenness of transparent work WK2 shown in FIG. 12A can also be detected as a shape image as shown in FIG. 12B.

Relations and characteristics of the images are shown in FIGS. 13A to 17B. Raw images of four phases obtained by imaging, from the X direction, a transparent film having gloss on the surface as work WK3 are shown in FIG. 13A. Raw images of four phases obtained by imaging the transparent film from the Y direction are shown in FIG. 13B. A specular reflection image showing a specular reflection component obtained from these raw images is shown in FIG. 14A. A diffuse reflection image showing a diffuse reflection component is shown in FIG. 14B. A normal image (an average image) for comparison is shown in FIG. 14C.

Specular Reflection Image

Figure 14A:
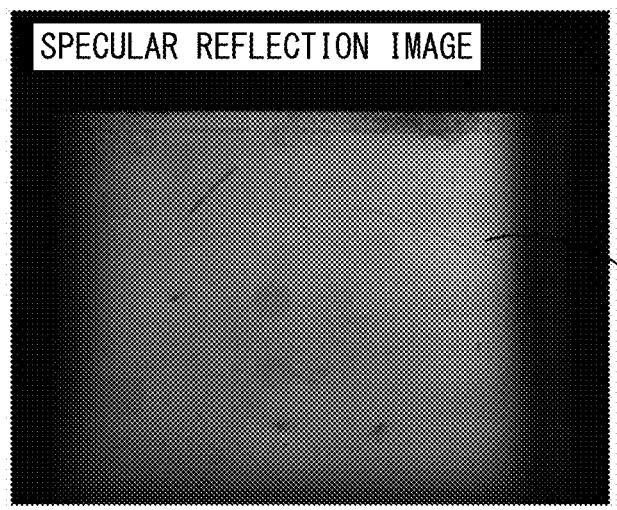
FIG. 14A is an image diagram showing a specular reflection image obtained from FIGS. 13A and 13B.
Figure 14B:
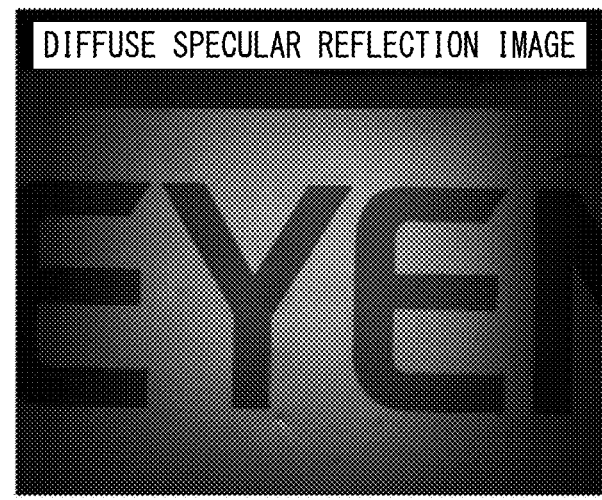
FIG. 14B is an image diagram showing a diffuse reflection image.
Figure 14C:
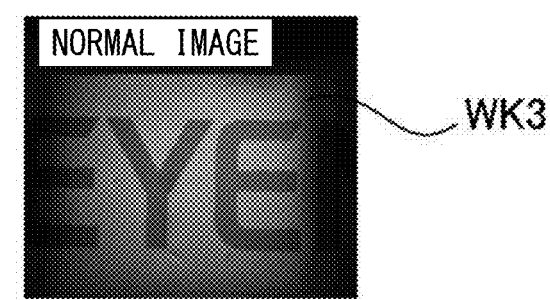
FIG. 14C is an image diagram showing a normal image.

As it is seen from the comparison with the normal image shown in FIG. 14C, from the specular reflection image shown in FIG. 14A, a stain that dulls specular reflection, a flaw that does not have a shape change but dulls specular reflection, a flaw that prevents the specular reflection because of a shape change, or the like is easily confirmed.

Diffuse Reflection Image

On the other hand, from the diffuse reflection image shown in FIG. 14B, a state of texture on the surface is easily confirmed.

Gloss Ratio Image

A gloss ratio image showing a ratio of specular reflection and diffuse reflection obtained from FIGS. 14A and 14B is shown in FIG. 15. In the gloss ratio image, a place where only either one of the specular reflection and the diffuse reflection intensely changes when a stripe is shifted is emphasized.

On the other hand, a phase X image showing a shift of a phase in the X direction obtained from FIG. 13A is shown in FIG. 16A. A phase Y image showing a shift of a phase in the Y direction obtained from FIG. 13B is shown in FIG. 16B. As shown in these figures, it is seen that a shape change appears as the shift of the phase.

Shape Image

Figure 17A:
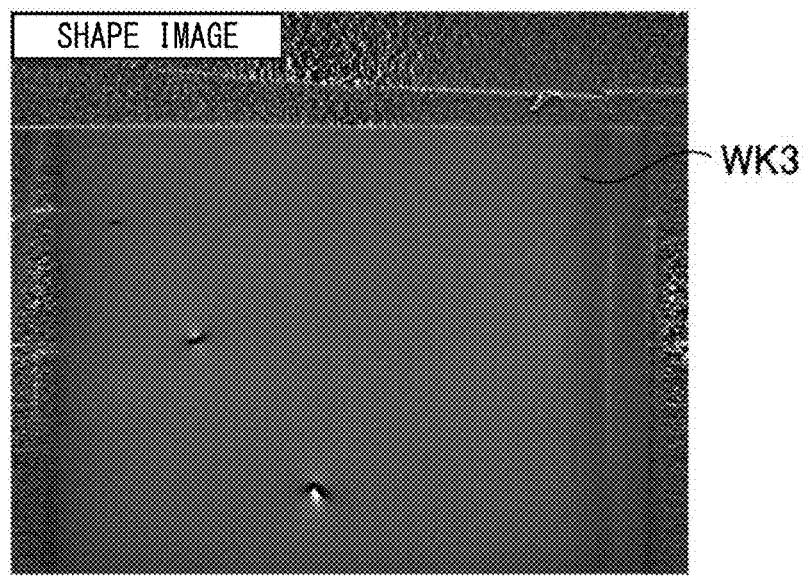
FIG. 17A is an image diagram showing a shape image obtained from FIGS. 16A and 16B.
Figure 17B:
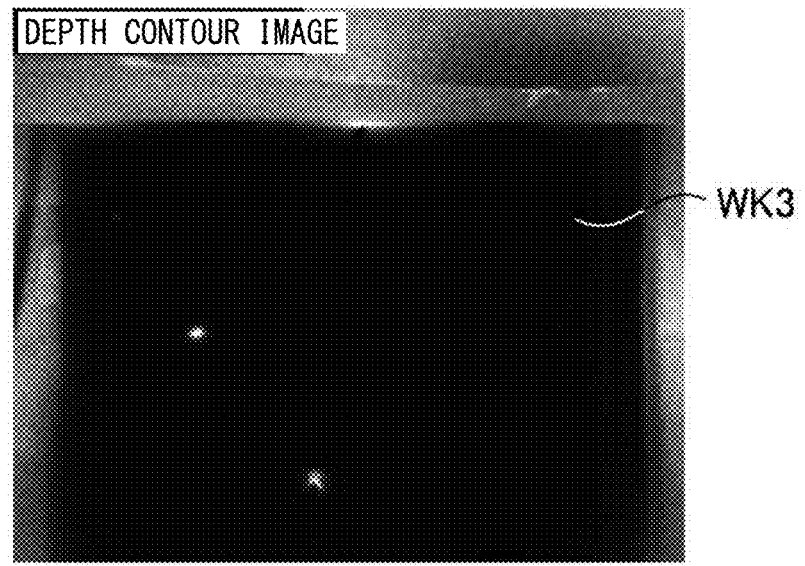
FIG. 17B is an image diagram showing a depth contour image obtained from FIGS. 16A and 16B.

A shape image obtained from FIGS. 16A and 16B is shown in FIG. 17A. A depth contour image obtained from FIGS. 16A and 16B is shown in FIG. 17B. In the shape image shown in FIG. 17A, changes of phases are stacked while viewing peripheral pixels according to the characteristic size. When the characteristic size is set large, unevenness relatively shallow and having a wide area in a shape change can be grasped. On the other hand, when the characteristic size is set small, a line flaw and a flaw having a small area are grasped. Further, when the shape image shown in FIG. 17A is compared with the specular reflection image shown in FIG. 14A, it can be confirmed that a defect (e.g., a thin flaw or a deep flaw) not appearing in the shape image tends to appear in the specular reflection image.

Depth Contour Image

In the depth contour image shown in FIG. 17B, a reference plane is calculated and a shift from the plane is imaged. From the depth contour image, it is possible to grasp a line flaw and a flaw having a small area.

Procedure for setting imaging conditions using the line camera.

Figure 18:
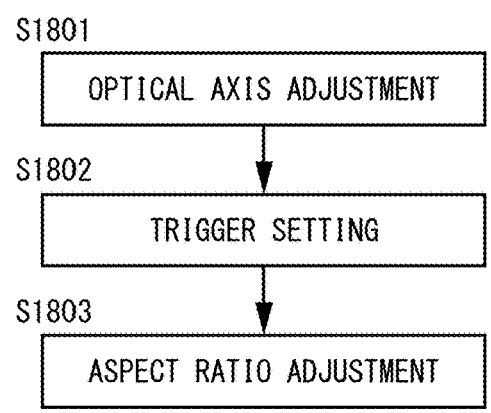
FIG. 18 is a flowchart for explaining a procedure for setting imaging conditions using a line scan camera.

Setting of the line camera is considered difficult compared with the normal area camera in which imaging elements are two-dimensionally arranged. This is because, for example, optical axis adjustment is strict and not only start timing of imaging but also an imaging interval for specifying an imaging interval with respect to feeding speed of work has to be appropriately set. In particular, in setting of a line scan interval, which is an imaging interval of a line scan camera, there are conditions peculiar to the line camera different from the area camera. That is, in the area camera, since imaging elements are usually arranged at equal interval longitudinally and laterally, longitudinal and lateral pixel resolutions are physically fixed to 1:1. On the other hand, in the line camera, as shown in FIG. 3, the imaging elements are arranged in one direction (the X direction). The Y direction is determined by conveying speed of work and imaging timing (line scan interval) of the imaging elements. In general, in an image inspection such as a flaw inspection, the sizes of a flaw are different longitudinally and laterally unless an aspect ratio, that is, pixel resolutions in the X direction and the Y direction are set to 1:1. In general, the conveying speed of work is a given value (a fixed value) that cannot be controlled on the image inspection apparatus side. Therefore, the conveying speed of work has to be adjusted by imaging timing, that is, a line scan interval. However, since an obtained image originally has a linear shape, that is, a line shape in the line camera, it is difficult to determine the conveying speed from the obtained image. It is not easy to adjust the conveying speed. Therefore, the image inspection apparatus 100 according to this embodiment has a function of guiding setting work of the imaging section 10 such that such troublesome setting work can be easily performed. As the setting work guidance function for imaging conditions, for example, it is conceivable to guide the setting work while navigating items that should be set. In the following explanation, a procedure for setting the imaging conditions using the line camera is explained with reference to a flowchart of FIG. 18.

First, in step S1801, the image inspection apparatus performs optical axis adjustment of the camera section and the illuminating section. In a state in which the work is stopped, images are repeatedly captured by the line camera to generate an image for optical axis adjustment having periodicity in the line direction and the optical axis adjustment is performed on the image for optical axis adjustment. For example, an optical axis adjustment screen 110 of an image inspection program shown in FIG. 19 is displayed on a screen of the display section 50.

Optical Axis Adjustment Screen 110

The optical axis adjustment screen 110 configures a form of an optical axis adjusting section for adjusting the optical axis of the line camera in a state in which an image obtained by imaging work in a standstill state with the line camera is displayed on the display section. The optical axis adjustment screen 110 includes a setting field 111 (the left side in FIG. 19) and an image display field 112 (the right side in FIG. 19). In the setting field 111, a title field 113 showing a stage of navigation and an explanation field 114 of setting content that should be performed in the setting field 111 are provided. In the title field 113, adjustment of the optical axis is displayed in a first stage of three stages shown as "STEP ⅓ optical axis adjustment". In the explanation field 114, "Optical axis setting of the camera and the illumination is performed. Please adjust the focus and the brightness to be equal on the left and the right while comparing the left and the right of the image" is displayed. Further, in the setting field 111, setting items that should be performed in the optical axis adjustment screen 110 are enumerated. Basically, the optical axis adjustment screen 110 is configured to cause the user to set parameters of imaging conditions from the upper stage toward the lower stage. Consequently, the user can sequentially perform the necessary setting in a designated procedure. The user is guided without hesitating about the setting.

Figure 19:
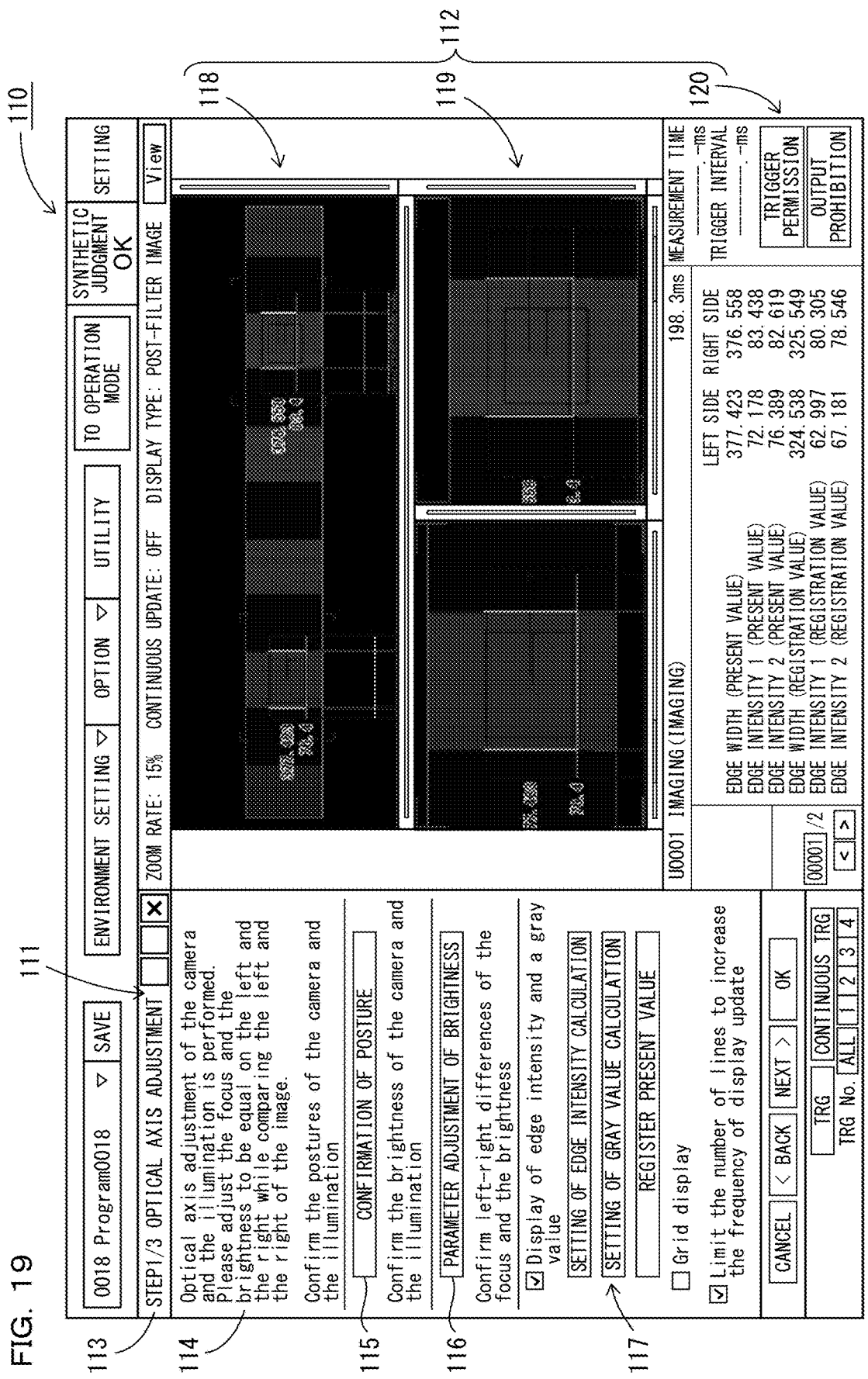
FIG. 19 is an image diagram showing an optical axis adjustment screen of an image inspection program.

In the setting field 111 shown in FIG. 19, a "posture confirmation" button 115 for confirming postures of the camera section and the illuminating section, a "brightness parameter adjustment" button 116 for adjusting brightness of the camera section and the illuminating section, and a confirmation field 117 for confirming a focus and brightness on the left and the right are provided. In the confirmation field 117, an "edge intensity calculation setting" button, a "gray value calculation setting" button, and a "present value registration" button are provided. The user determines rough postures of the camera section and the illuminating section using the "posture confirmation" button 115. The user changes setting values of imaging conditions such as shutter speed, camera sensitivity, and illumination volume and adjusts brightness using the "brightness parameter adjustment" button 116. Further, the user finely adjusts setting conditions for the camera section and the illuminating section to prevent a left-right difference from occurring in the focus and the brightness. When finely adjusting the setting conditions, the user sets the items while slightly moving around in the setting field 111 to, for example, return to the former adjustment of brightness and repeat the adjustment.

In such a flow of the optical axis adjustment, it is possible to display the postures of the camera section and the illuminating section and register the postures at that time. Saved data is retained in the storing section 32 and read out when necessary.

In the image display field 112, a full image display region 118, a left/right enlarged display region 119, and an information display region 120 are provided. In the left/right enlarged display section 119 in the middle stage, a part of an image displayed in the full image display region 118 is enlarged and displayed. In the information display region 120 in the lower stage, parameters concerning a currently displayed raw image are displayed. In this example, an edge width, edge intensity 1, edge intensity 2, a concentration average, maximum concentration, minimum concentration, and the like are displayed.

Since the full image display region 118 and the left/right enlarged display region 119 are provided, it is possible to enlarge and display an overall image of imaging target work and the left and the right of the imaging target in the same screen. Whereas it is necessary to adjust the camera section and the illuminating section to prevent a left-right difference in brightness and a focusing state, it is possible to make it easy to confirm the left-right difference by arranging the overall image of the imaging target work and the left and the right of the imaging target side by side on one screen in this way.

Visual confirmation is facilitated in the left/right enlarged display region 119. In addition, since the edge intensity and the gray value are displayed as numerical values in the information display region 120, it is possible to confirm the left-right difference as a numerical value as well. Further, since the edge intensity is displayed as the numerical value, it is possible to easily display a peak of a focus.

Trigger Setting Screen 121

Figure 20:
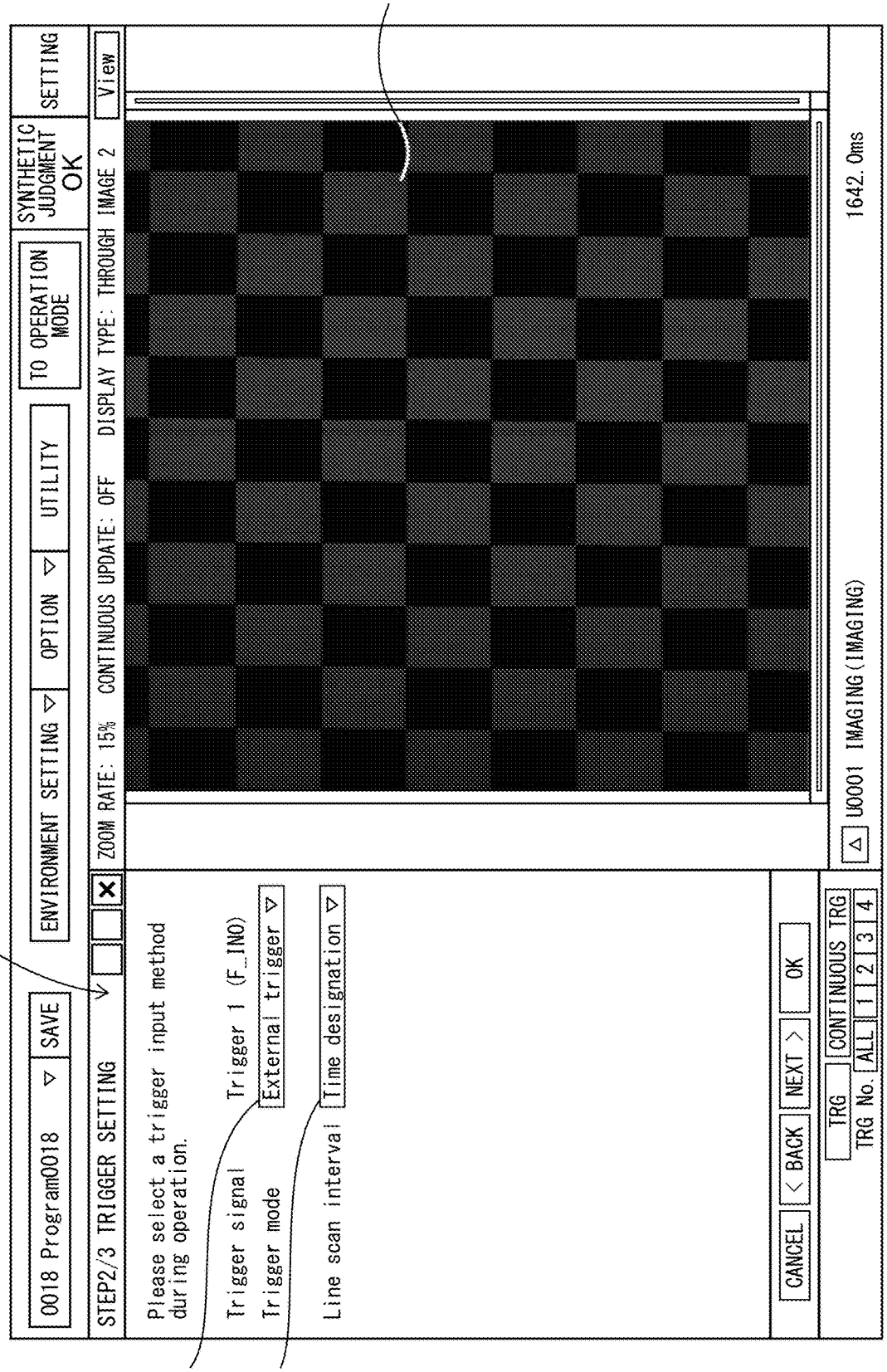
FIG. 20 is an image diagram showing a trigger setting screen of the image inspection program.

When the adjustment of the optical axis is ended in step S1801 as explained above, subsequently, the image inspection apparatus performs trigger setting in step S1802. The trigger setting is performed by a trigger setting section. The trigger setting section sets a trigger for specifying timing for imaging work with the line camera. As a form of the trigger setting section, an input method of a trigger during operation is selected from a trigger setting screen 121 of the image inspection program shown in FIG. 20. Specifically, the trigger setting section performs setting from a trigger mode setting field 122 for setting a trigger mode for determining timing of imaging and a line scan interval setting field 123 for setting an interval of line scan provided in the setting field 111. In the trigger mode setting, the trigger setting section selects whether the trigger is set to an external trigger input from the outside or an internal trigger specified on the inside of the image inspection apparatus. The trigger setting section selects, as a line scan interval, whether an input from the work conveying mechanism side for conveying the work, for example, an output of a rotary encoder provided in a rotating shaft of a conveyor is used for imaging timing of one line or a time interval is designated and one line is imaged in every fixed time.

Aspect Ratio Adjustment Screen 130

Figure 21:
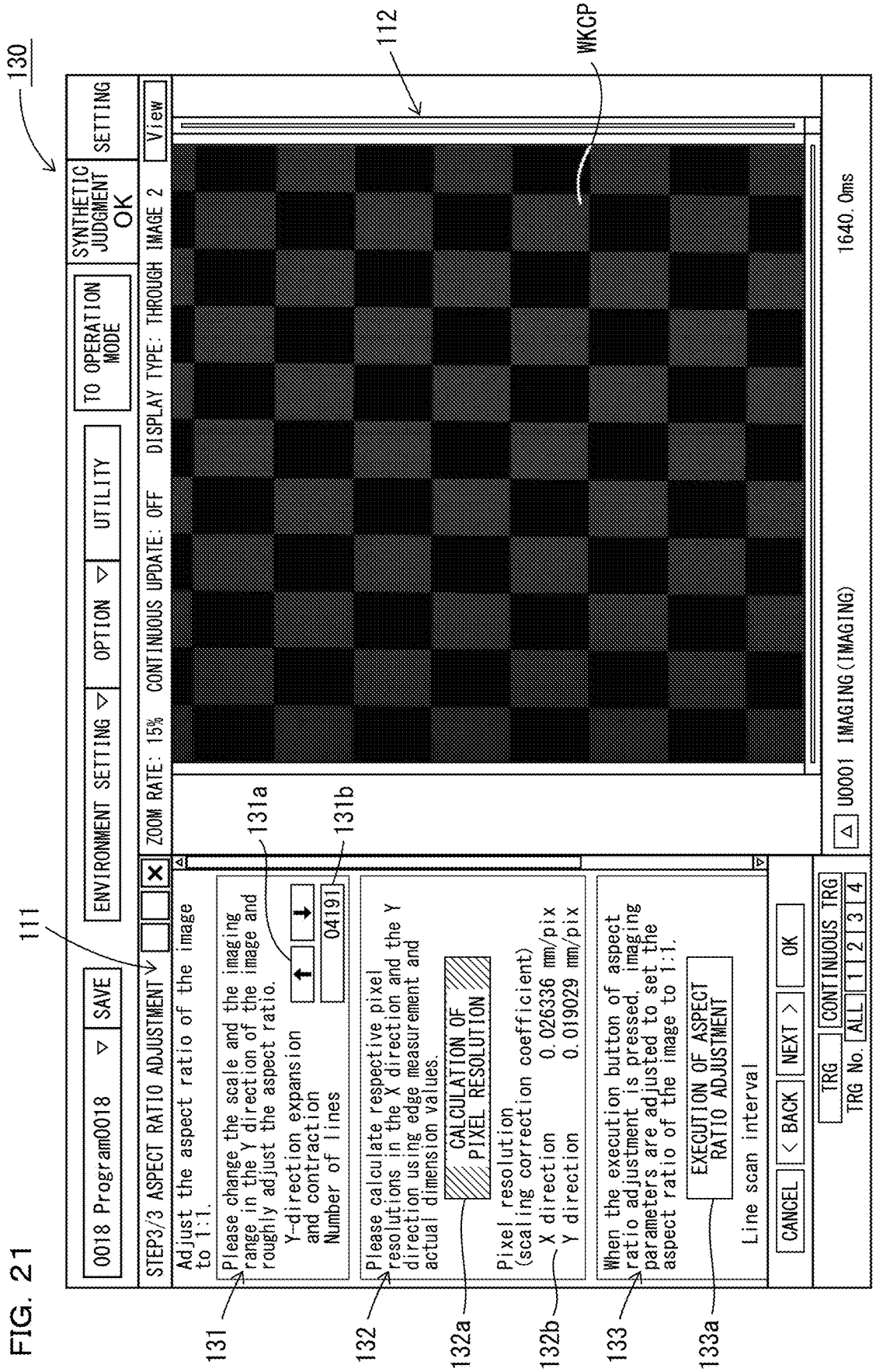
FIG. 21 is an image diagram showing an aspect ratio adjustment screen of the image inspection program.
Figure 22:
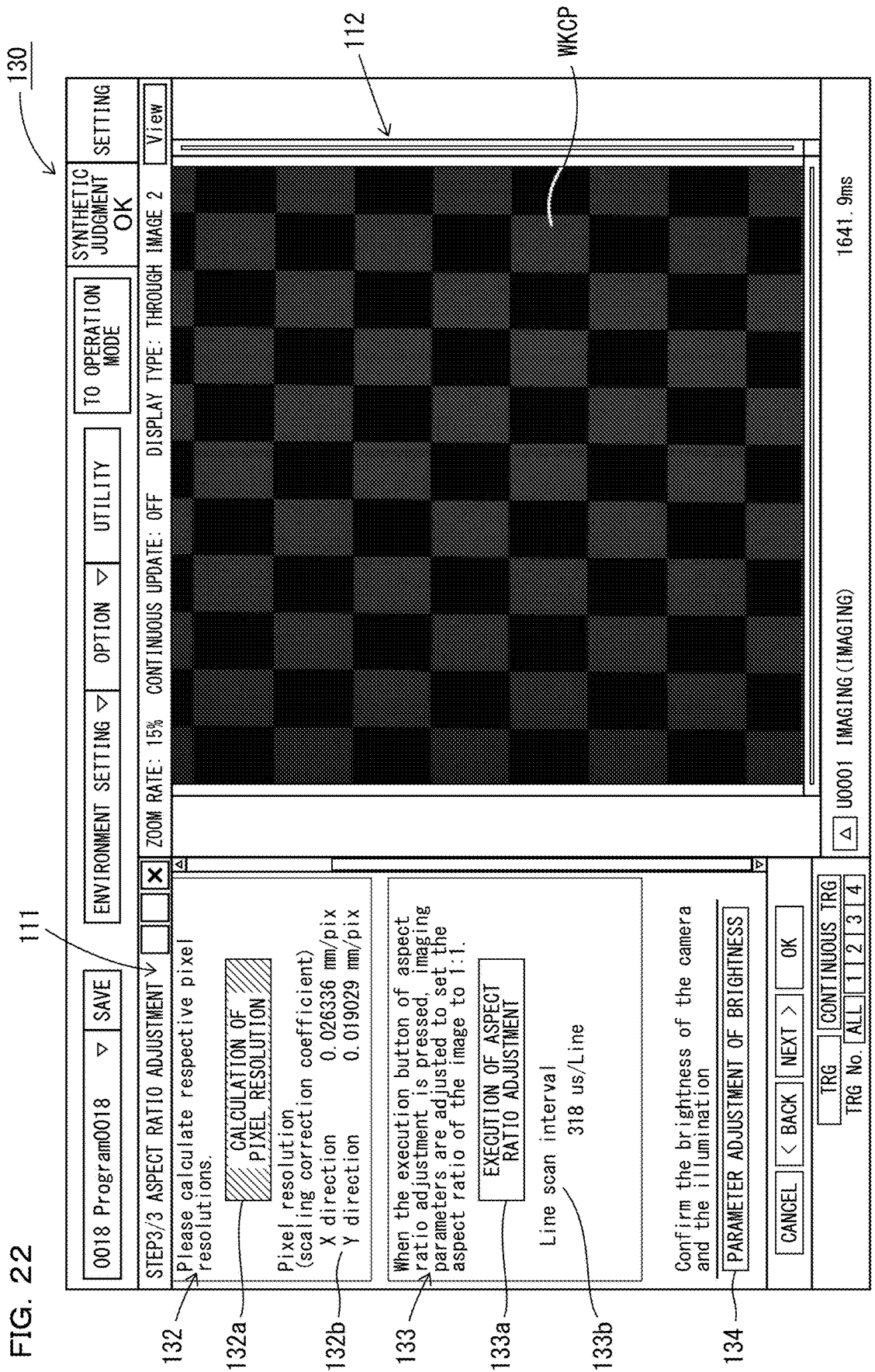
FIG. 22 is an image diagram showing a state in which the aspect ratio adjustment screen in FIG. 21 is scrolled in the downward direction.

Lastly, in step S1803, the image inspection apparatus performs adjustment of an aspect ratio of the image. The aspect ratio adjustment is scaling correction for calculating pixel resolution and correcting the pixel resolution to set the aspect ratio of the image to 1:1. The aspect ratio adjustment can be performed on an aspect ratio adjustment screen 130 of the image inspection program shown in FIGS. 21 and 22. The aspect ratio adjustment screen 130 is a form of an aspect ratio adjusting section for adjusting longitudinal and lateral pixel resolutions of an image captured by the line camera. Note that FIG. 22 shows a state in which the setting field 111 is scrolled in the downward direction in the aspect ratio adjustment screen 130 shown in FIG. 21. A line scan interval in the Y direction is adjusted according to the X direction from the aspect ratio adjustment screen 130 of the image inspection program shown in FIGS. 21 and 22 such that longitudinal and lateral pixel resolutions of the image coincide. The user moves the work conveying mechanism WC to actually move the work, irradiates illumination light with the illuminating section, and images the work with the imaging section. In this case, as the work, it is desirable to use work on which a predetermined pattern is displayed. For example, work WKCP on which a checker pattern having known size shown in the image display field 112 in FIGS. 21 and 22 is displayed is used. In the checker pattern of the work WKCP, white and black square rectangles are alternately disposed. Therefore, the user adjusts imaging parameters to set an aspect ratio of the checker pattern to 1:1 while displaying an obtained raw image in the image display field 112.

Sub-Process Setting Field

In an aspect ratio adjustment process, it is possible to further cause the user to set parameters necessary in a predetermined procedure. For example, as sub-processes configuring the aspect ratio adjustment process, a rough expansion and contraction process in the Y direction, a calculation process for pixel resolutions in the X direction and the Y direction, and an adjustment process for the imaging parameters are included in the aspect ratio adjustment process. In the example of the aspect ratio adjustment screen 130 shown in FIGS. 21 and 22, three sub-process setting fields are arranged in setting order and displayed from up to down in the setting field 111. Consequently, the user is guided to be capable of executing the aspect ratio adjustment process by setting the setting field 111 from up to down. In the setting field 111 shown in FIG. 21, a Y-direction expansion and contraction field 131 corresponding to the rough expansion and contraction process in the Y direction, a pixel resolution calculation field 132 corresponding to the calculation process for pixel resolutions in the X direction and the Y direction, and an imaging parameter adjustment field 133 corresponding to the adjustment process for the imaging parameters are provided in order from the top.

Longitudinal Direction Expanding and Contracting Section

The Y-direction expansion and contraction field 131 is a form of a longitudinal direction expanding and contracting section for expanding and contracting, in the longitudinal direction, an image obtained by the imaging of the line camera. The longitudinal direction expanding and contracting section adjusts an aspect ratio of the image by roughly changing an imaging interval of the line camera.

Y-Direction Expansion and Contraction Field 131

In the Y-direction expansion and contraction field 131, a scale and an imaging range in the Y direction of the image corresponding to the conveying direction of the work is changed to roughly adjust the aspect ratio. An expansion button 131a for adjusting expansion and contraction in the Y direction and a number-of-lines setting field 131b for specifying the number of lines are provided. In this example, the expansion button 131a is configured by up and down arrow buttons. When an upward arrow is pressed, it is possible to expand the image in the longitudinal direction. Conversely, when a downward arrow is pressed, it is possible to contract the image. The user roughly adjusts expansion and contraction in the Y direction while viewing the checker pattern displayed in the image display field 112. Display content in the image display field 112 is changed on a real-time basis according to setting in the Y-direction expansion and contraction field 131.

Pixel Resolution Calculation Field 132

In the pixel resolution calculation field 132, edge measurement and actual dimension values are compared to calculate correction coefficients (scaling correction coefficients) of respective pixel resolutions in the X direction and the Y direction. In the example shown in FIGS. 21 and 22, a pixel resolution calculation button 132a is provided. When the pixel resolution calculation button 132a is pressed, the aspect ratio adjustment screen 130 is transitioned to pixel resolution calculation screens 160X and 160Y shown in FIGS. 23 and 24.

Pixel Resolution Calculating Section

The pixel resolution calculation screens 160X and 160Y are a form of a pixel resolution calculating section that calculates pixel resolutions in the longitudinal direction and the lateral direction of an image captured by the line camera. The pixel resolution calculating section calculates pixel resolutions respectively in the X direction and the Y direction.

Pixel Resolution Calculation Screens 160X and 160Y

Figure 23:
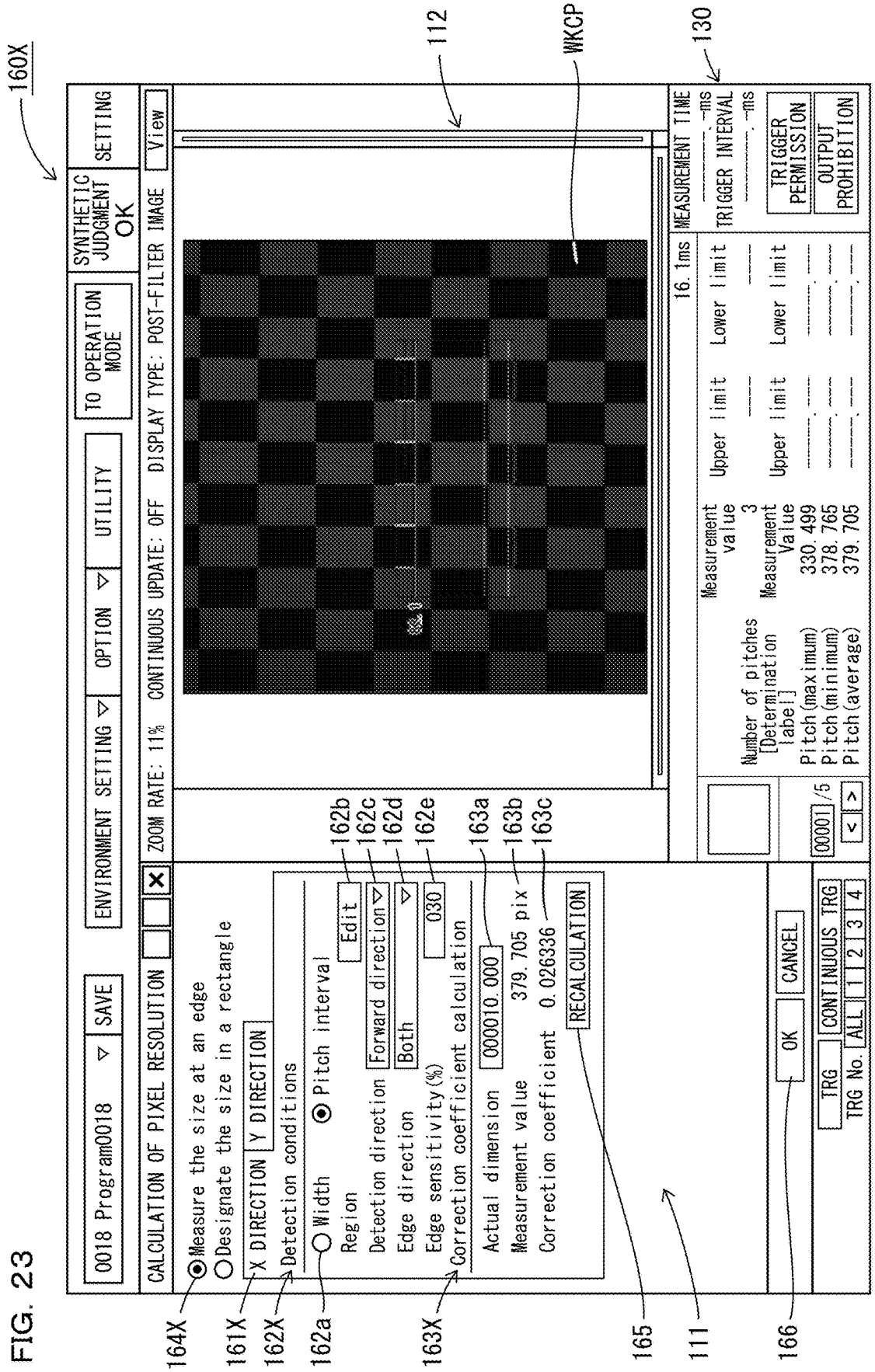
FIG. 23 is an image diagram showing a pixel resolution calculation screen for calculating pixel resolution in the X direction.
Figure 24:
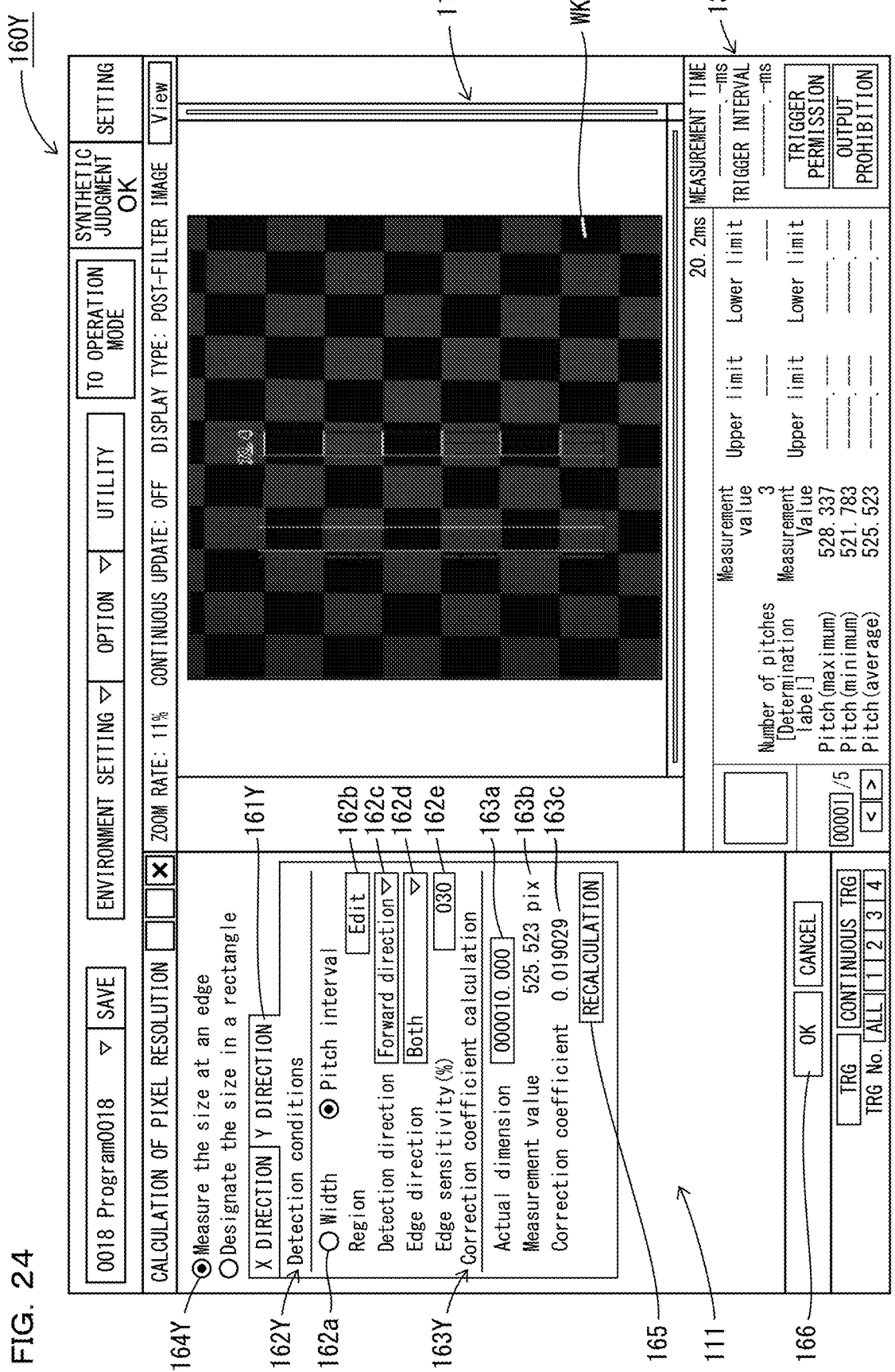
FIG. 24 is an image diagram showing a pixel resolution calculation screen for calculating pixel resolution in the Y direction.

FIG. 23 shows the pixel resolution calculation screen 160X for calculating pixel resolution in the X direction. FIG. 24 shows the pixel resolution calculation screen 160Y for calculating pixel resolution in the Y direction. These screens can be switched by an "X-direction" tab 161X and a "Y-direction" tab 161Y provided in the setting field 111. In the "X-direction" tab 161X and the "Y-direction" tab 161Y of the setting field 111, extraction condition setting fields 162X and 162Y for detecting pixel resolutions and correction coefficient calculation fields 163X and 163Y for calculating correction coefficients in calculating the pixel resolutions are respectively provided.

In the calculation of the pixel resolutions, it is possible to select whether size is measured at an edge or size is designated in a rectangle. In the pixel resolution calculation screens 160X and 160Y shown in FIGS. 23 and 24, these size designations are performed from size selection fields 164X and 164Y. According to the designation in the size selection fields 164X and 164Y, extraction conditions for a region designated in the image display field 112 are designated from the extraction condition setting fields 162X and 162Y. A region used for the calculation of pixel resolutions is displayed on the image display field 112. Further, the information display region 120 is provided below the image display field 112. The measured number of pitches, a maximum, a minimum, and an average of the pitches, a measurement time, a trigger interval, and the like are displayed.

In the extraction condition setting fields 162X and 162Y, a width/pitch interval selection field 162a for selecting whether the calculation of pixel resolutions is performed in width or performed in a pitch interval, an editing button 162b for editing a designated region, a detection direction designation field 162c for designating a detection direction, an edge direction designation field 162d for designating an edge direction, an edge sensitivity designation field 162e for designating edge sensitivity, and the like are provided.

In the correction coefficient calculating fields 163X and 163Y, an actual dimension designation field 163a for inputting actual dimension values of the checker pattern of the work WKCP as numerical values, a measurement value display field 163b for displaying a measured dimension as the number of pixels, a correction-coefficient display field 163c for displaying a calculated pixel resolution correction coefficient (a scaling correction coefficient), and the like are provided. Further, a recalculation button 165 for recalculating a pixel resolution when the extraction conditions and the like are changed is provided.

Pixel resolution correction coefficients (scaling correction coefficients) are respectively calculated in the X direction and the Y direction according to the setting in the pixel resolution calculation screens 160X and 160Y. After confirming the calculated numerical values in the correction coefficient display field 163c, when the user presses an "OK" button 166, the pixel resolution calculation screens 160X and 160Y return to the aspect ratio adjustment screen 130 shown in FIGS. 21 and 22. The calculated scaling correction coefficients are displayed in a pixel resolution calculation result display field 132b. In the example shown in FIGS. 21 and 22, the calculated pixel resolutions in the X direction and the Y direction are displayed as X direction 1 mm/pixel and Y direction 1 mm/pixel.

Imaging Parameter Adjusting Section

The imaging parameter adjustment field 133 is a form of an imaging parameter adjusting section for adjusting imaging parameters specifying imaging conditions of the line camera. The imaging parameter adjusting section calculates an imaging interval of the line camera for setting the pixel resolution in the longitudinal direction and the pixel resolution in the lateral direction to a desired ratio and reflects the imaging interval on the imaging parameters.

Imaging Parameter Adjusting Field 133

Figure 25:
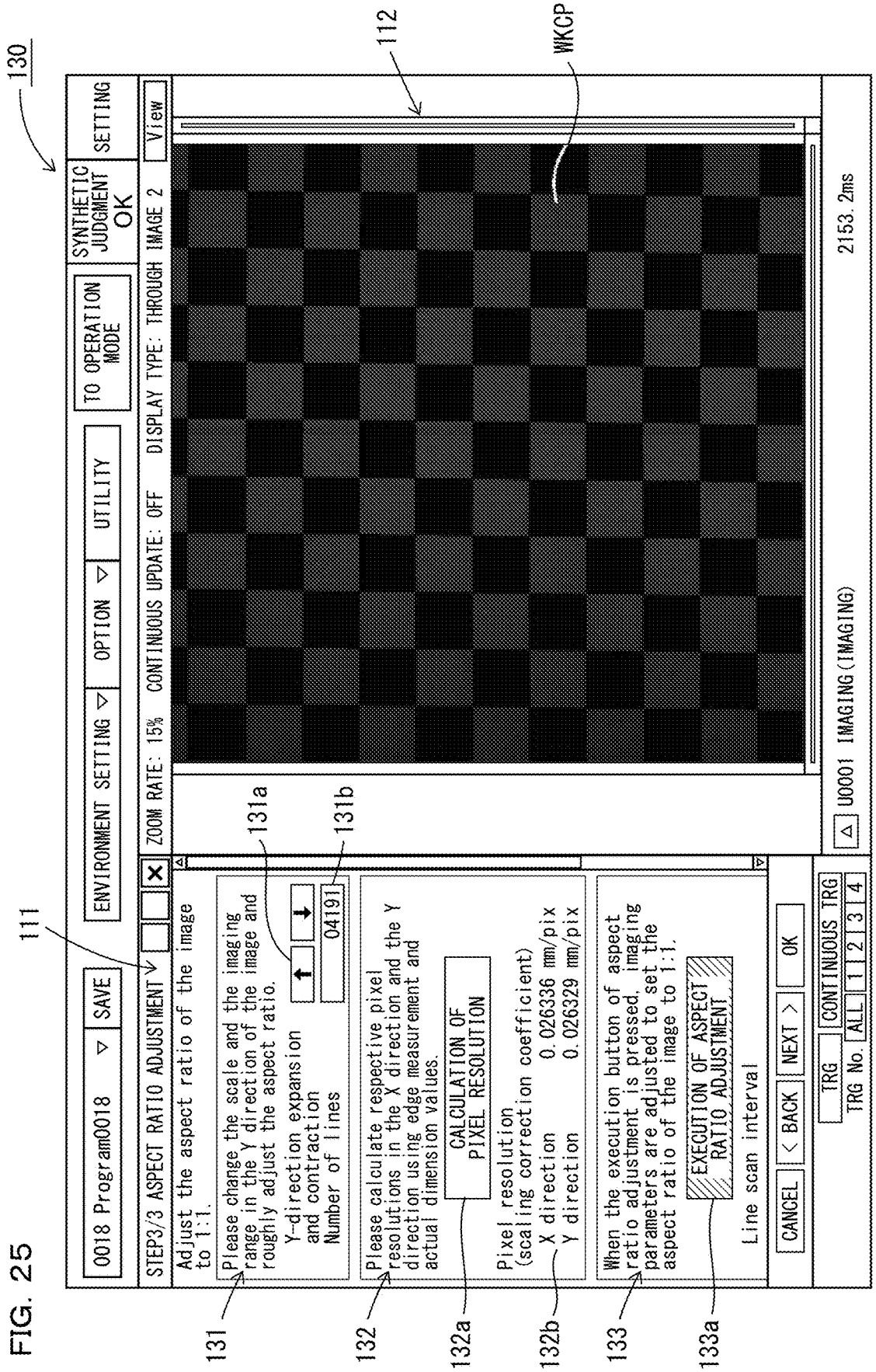
FIG. 25 is an image diagram showing a result obtained by adjusting an aspect ratio on the aspect ratio adjustment screen shown in FIG. 21.
Figure 26:
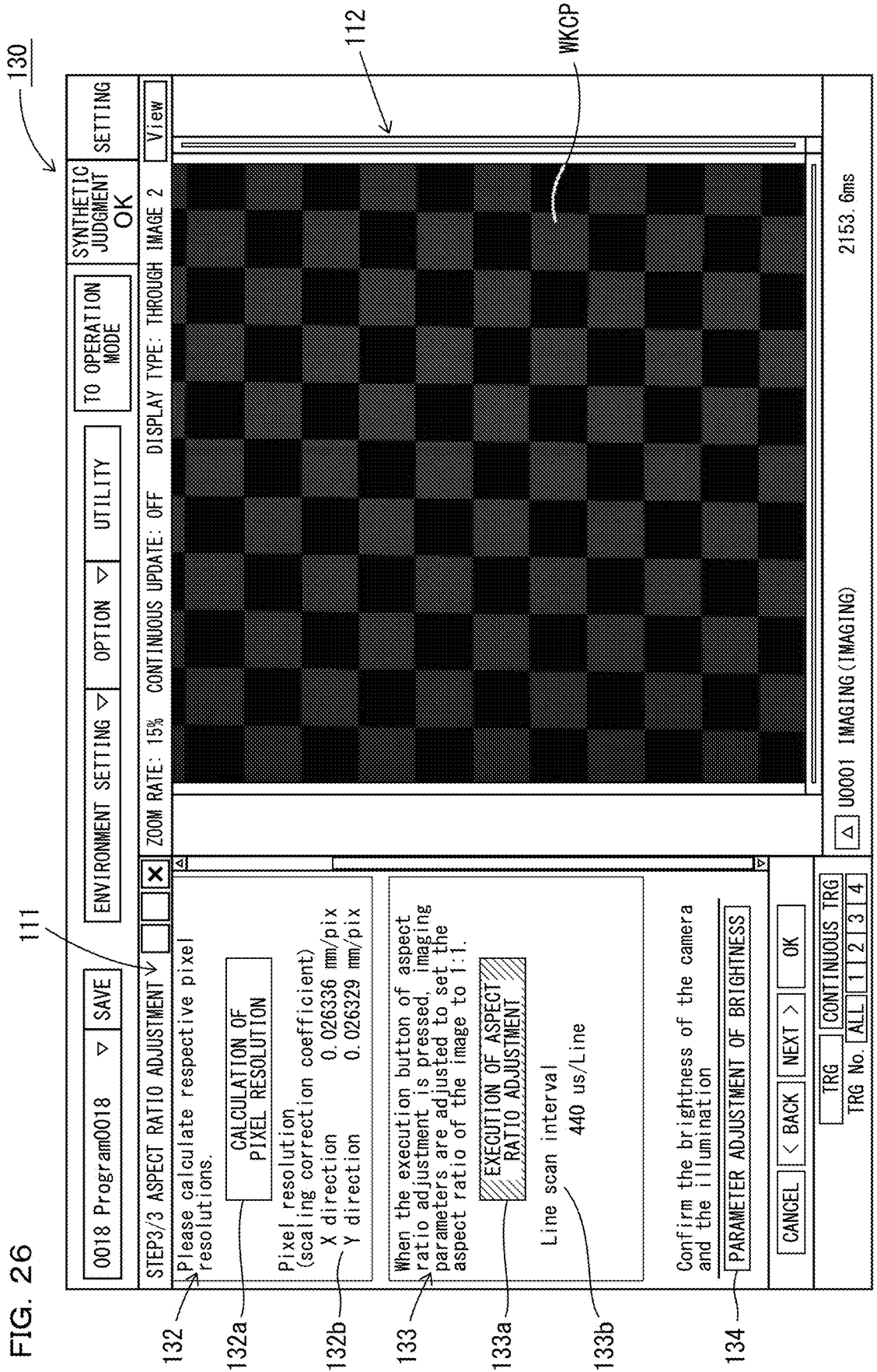
FIG. 26 is an image diagram showing a result obtained by adjusting an aspect ratio on the aspect ratio adjustment screen shown in FIG. 22.

In the imaging parameter adjusting field 133, the imaging parameters are adjusted to set the aspect ratio of the image to 1:1. As shown in FIG. 22, an aspect ratio adjustment execution button 133a and an imaging parameter adjustment result display field 133b are provided. When the aspect ratio adjustment execution button 133a is pressed, imaging parameters for setting the aspect ratio of the image to 1:1 are automatically calculated and adjusted to the value. When the aspect ratio adjustment execution button 133a is pressed and the automatic adjustment of the imaging parameters is executed, a result of the automatic adjustment is displayed in the imaging parameter adjustment result display field 133b. A line scan interval after the imaging parameter adjustment is displayed. Further, the work WKCP of the image display field 112 is drawn again on the image adjusted to set the aspect ratio to 1:1. That is, the aspect ratio adjustment screen 130 shown in FIG. 21 is updated to FIG. 25. The aspect ratio adjustment screen 130 shown in FIG. 22 is updated to FIG. 26.

As explained above, the image inspection apparatus 100 causes the user to perform the setting of imaging conditions, which has been considered complicated, while guiding the user in a navigation scheme. Further, in the aspect ratio adjustment screen 130, a brightness parameter adjusting section 134 for adjusting the brightness of the camera and the illumination is provided.

Posture Display Function

The image inspection apparatus 100 includes a posture display function for visually displaying the postures of the imaging section 10 and the illuminating section 20. As an example of the posture display function, in the optical axis adjustment screen 110 shown in FIG. 19 explained above, when the "posture confirmation" button 115 is pressed, a camera posture display screen 140 of the image inspection program shown in FIG. 27 and an illumination posture display screen 150 shown in FIG. 28 are displayed. Note that the camera posture display screen 140 shown in FIG. 27 and the illumination posture display screen 150 shown in FIG. 28 are switched by selecting tabs in the upper left of the screens. Details of the camera posture display screen 140 and the illumination posture display screen 150 are explained below.

The camera posture display screen 140 and the illumination posture display screen 150 shown in FIGS. 27 and 28 include a function of displaying the postures of the camera section and the illuminating section. Specifically, schematic posture display fields 141 and 151 and posture information display fields 142 and 152 are provided. In the schematic posture display fields 141 and 151, the postures of the camera section and the illuminating section are respectively displayed as the imaging schematic view 143 and the illumination schematic view 153. In the posture information display fields 142 and 152, the postures and angles are displayed as characters and numerical values to correspond to the imaging schematic view 143 and the illumination schematic view 153 displayed in the schematic posture display fields 141 and 151. In order to realize such a posture display function, the camera section and the illuminating section are respectively mounted with two-axis gravitational acceleration sensors. The camera section and the illuminating section convert outputs of the gravitational acceleration sensors into inclination angles and cause the display section to display the inclination angles.

Camera Posture Display Screen 140

In the camera posture display screen 140, degrees of shifts from the gravity direction respectively with respect to the rear surface, the side surface, and the upper surface, which are reference postures of the camera section, are shown using the imaging schematic view 143 simulating the camera section and output as numerical values. As a form of display of the imaging schematic view 143, besides a form of displaying a plurality of, for example, three two-dimensional views shown in FIG. 27 and the like, one or a plurality of views may be stereoscopically displayed in a three-dimensional display forms such as a perspective view.

Note that, when a posture is detected using a two-axis gravitational acceleration sensor and the imaging schematic view 143 is displayed to be divided into the rear surface, the side surface, and the upper surface, depending on a posture, there is a surface from which useful information is not obtained. For example, in a surface perpendicular to the gravity, an angle formed between the surface and the gravity direction is unstable. Therefore, the visibility of the unstable surface may be reduced by, for example, reducing concentration not to give meaningless information to the user such that a meaningful surface attracts attention.

Figure 29:
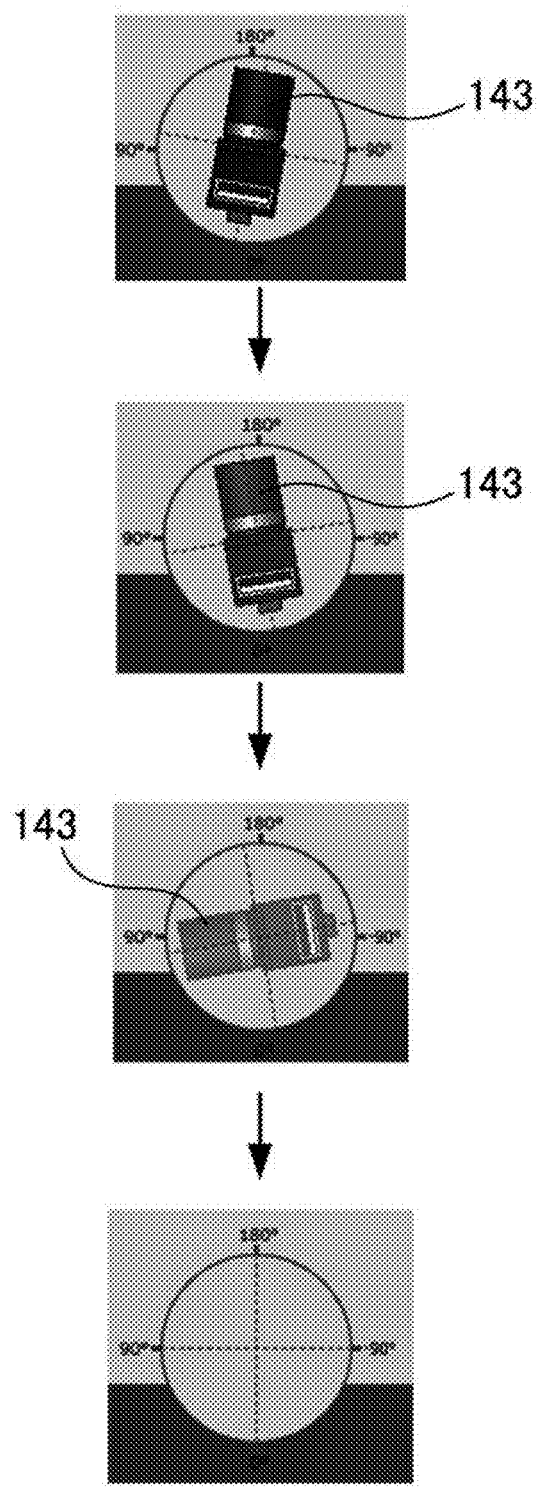
FIG. 29 is an image diagram showing a state in which a color of display is softened according to the magnitude of gravity received by a surface.

For example, as shown in FIG. 29, a color of a figure may be gradually softened according to the intensity of the gravity received by a certain surface among the surfaces configuring the camera section and may be hidden soon. When the gravity received by the surface is weak, a calculated angle is unstable and fluctuates. Therefore, the posture is seen excessively changed and sometimes gives uneasiness to the user. Therefore, to prevent a surface that should not attract attention from attracting more attention than a surface that should originally attract attention, such a situation can be avoided by softening the color of such a surface or not displaying the surface.

Illumination Posture Display Screen 150

Figure 30:
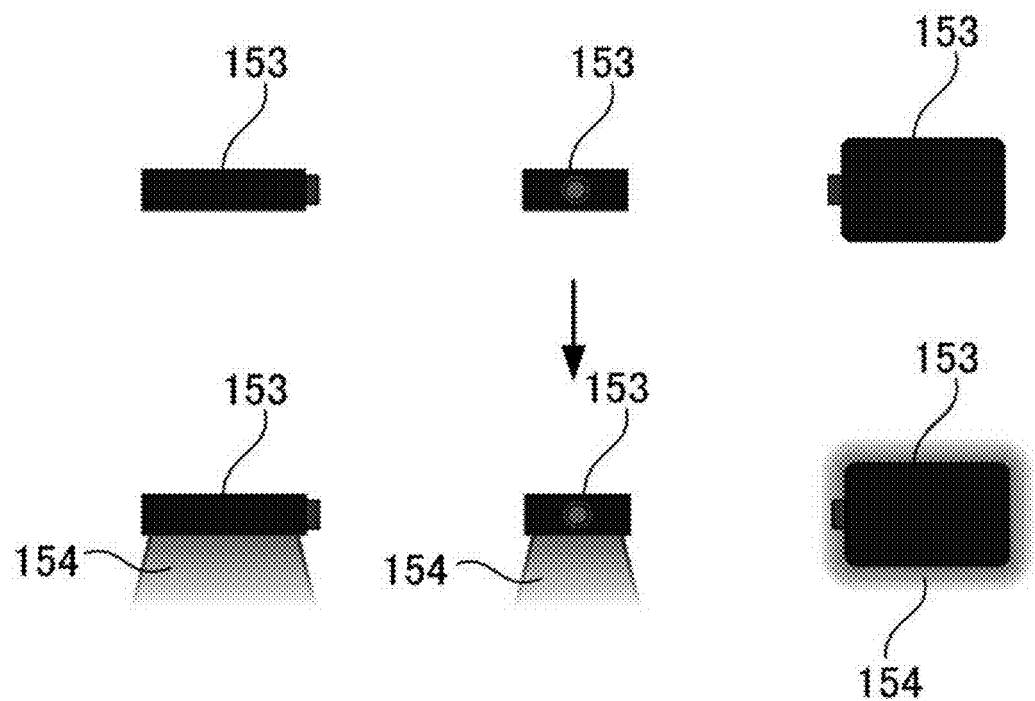
FIG. 30 is an image diagram showing an example in which illumination light is included in an illumination schematic view and displayed.

As the illumination posture display function, a basic function is the same as the camera posture display function explained above. The illumination posture display surface 150 shown in FIG. 28 shows the illumination schematic view 153 simulating the illuminating section. In general, the illuminating section has few exterior characteristics compared with the camera section and the like. Therefore, it is possible to improve visibility by including illumination light emitted by the illuminating section in the illumination schematic view 153 and displaying the illumination light as shown in FIG. 30. Consequently, the user viewing the illumination schematic view 153 can easily distinguish, from an illumination light schematic view 154, which surface is a light emitting surface among the surfaces configuring the illuminating section and grasp the posture of the illuminating section with this as a clue.

The camera posture display function and the illumination posture display function explained above can also register postures of the camera section and the illuminating section at a certain point in time and compare the postures with postures of the camera section and the illuminating section at the present point in time. For example, as reference postures, plane postures such as a front view, a rear view, a top view, a bottom view, a right side view, and a left side view or a perspective view and the like designated by the user are stored in the storing section 32 in advance.

When the postures at the present point in time change with respect to the registered postures of the camera section and the illuminating section, a warning may be emitted from the warning output section 35 on the screen of the image inspection apparatus or to an external device connected to the image inspection apparatus. Further, the user may be capable of adjusting a threshold of such warning emission. Alternatively, the user may be capable of adjusting timing for performing a check of the postures of the camera section and the illuminating section.

Figure 31:
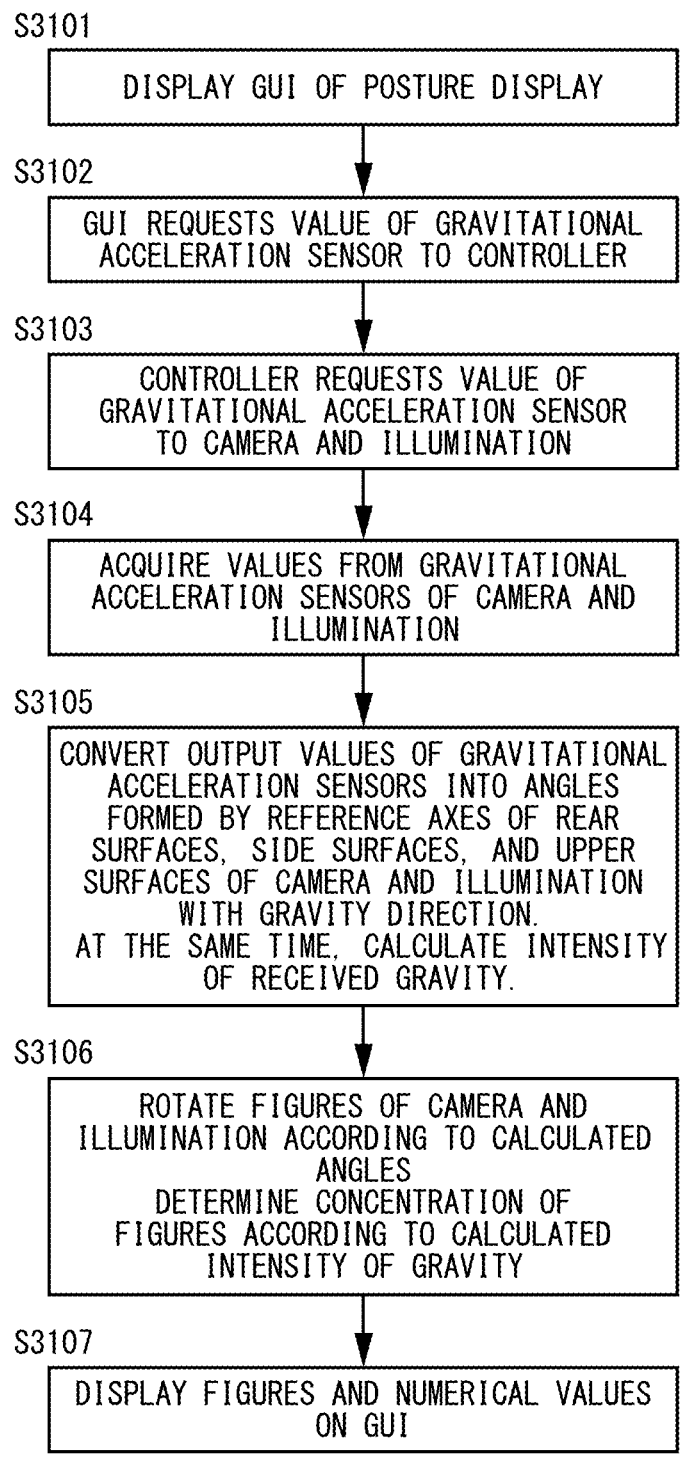
FIG. 31 is a flowchart for explaining a procedure for displaying postures of a camera section and an illuminating section on a screen.
Figure 32:
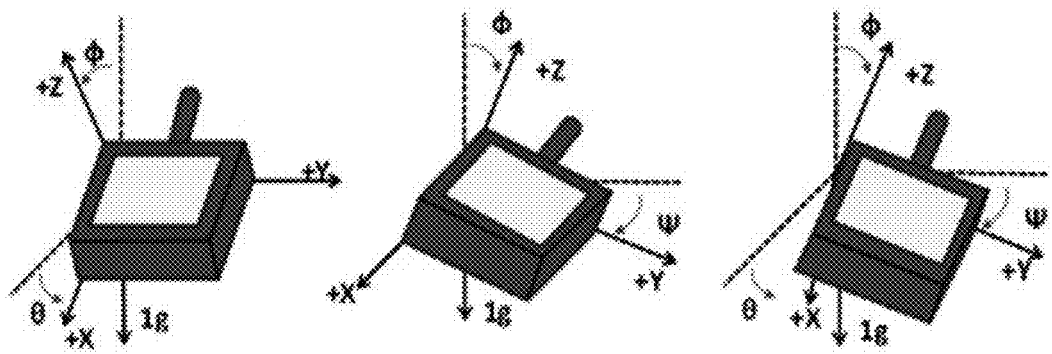
FIG. 32 is a perspective view showing an example of a GUI in which inclination states of the camera section and the illuminating section are displayed.
Figure 33A:
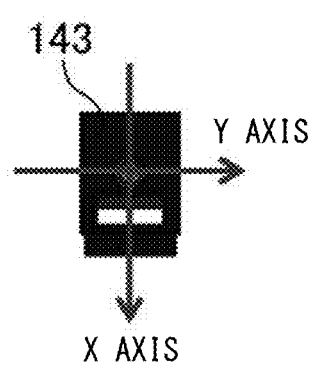
FIG. 33A is a plan view showing the rear surface of the camera section.
Figure 33B:
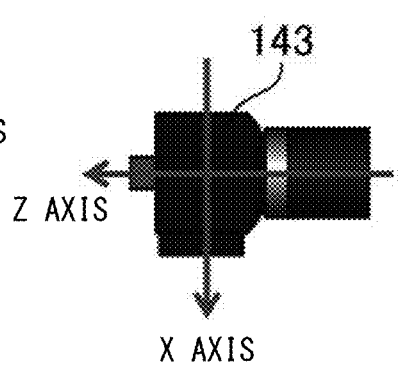
FIG. 33B is a plan view showing the side surface of the camera section.
Figure 33C:
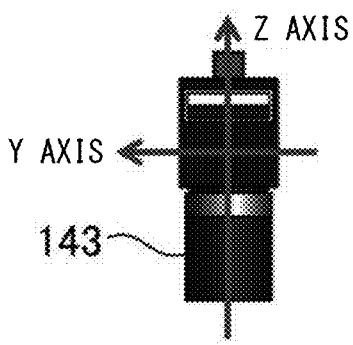
FIG. 33C is a plan view showing the upper surface of the camera section.
Figure 34A:
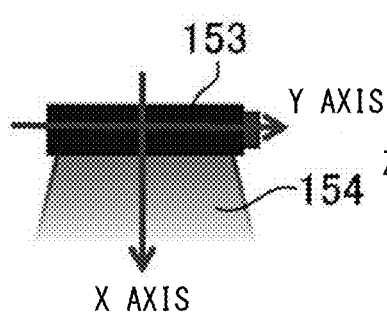
FIG. 34A is a plan view showing the rear surface of the illuminating section.
Figure 34B:
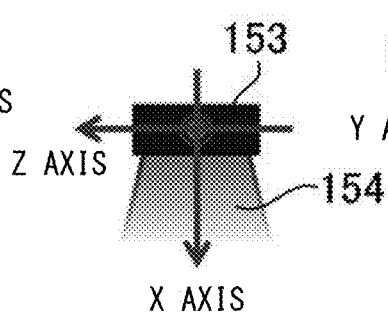
FIG. 34B is a plan view showing the side surface of the illuminating section.
Figure 34C:
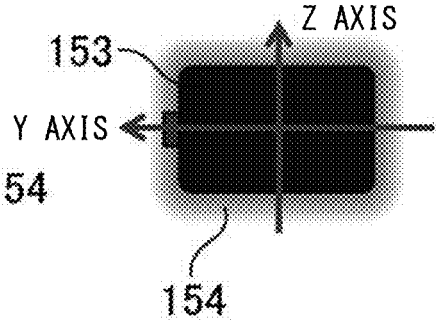
FIG. 34C is a plan view showing the upper surface of the illuminating section.

Procedure for Displaying the Postures of the Camera Section and the Illuminating Section on the Screen A procedure for displaying the postures of the camera section and the illuminating section on the screen is explained with reference to a flowchart of FIG. 31. First, in step S3101, the image inspection apparatus displays a GUI of posture display. For example, as shown in FIG. 32, inclination states of the camera section and the illuminating section are displayed such that measurement angles are seen. As shown in FIGS. 33A to 33C, plan views of the camera section are displayed to clearly display the X axis, the Y axis, and the Z axis. In this example, in FIG. 33A, the X axis and the Y axis can be clearly displayed by displaying the rear surface of the camera section. In FIG. 33B, the X axis and the Z axis can be clearly displayed by displaying the side surface of the camera section. Further, in FIG. 33C, the Y axis and the Z axis can be clearly displayed by displaying the upper surface of the camera section. Similarly, as shown in FIGS. 34A to 34C, the X axis, the Y axis, and the Z axis set in the illuminating section can be clearly displayed by displaying the illumination schematic view 153. In this example, in FIG. 34A, the X axis and the Y axis can be clearly displayed by displaying the rear surface of the illuminating section. In FIG. 34B, the X axis and the Z axis can be easily displayed by displaying the side surface of the illuminating section. Further, in FIG. 34C, the Y axis and the Z axis can be clearly displayed by displaying the upper surface of the illuminating section.

Subsequently, in step S3102, a value of the gravitational acceleration sensor is requested to the image inspection apparatus. In step S3103, the image inspection apparatus requests values of the gravitational acceleration sensors to the camera section and the illuminating section. Further, in step S3104, the image inspection apparatus acquires the values of the gravitational acceleration sensors from the camera section and the illuminating section. Further, in step S3105, the image inspection apparatus converts the output values of the gravitational acceleration sensors into angles formed by the reference axes of the rear surfaces, the side surfaces, and the upper surfaces of the camera section and the illuminating section with the gravity direction. At the same time, the image inspection apparatus calculates the intensity of the received gravity as well. In step S3106, the image inspection apparatus rotates the figures of the camera section and the illuminating section according to the calculated angles. Further, the image inspection apparatus determines concentrations of the figures according to the calculated intensity of the gravity. Lastly, in step S3107, the image inspection apparatus displays the figures and the numerical values on the display section 50 as GUIs.

Posture Change Warning Function

Figure 35:
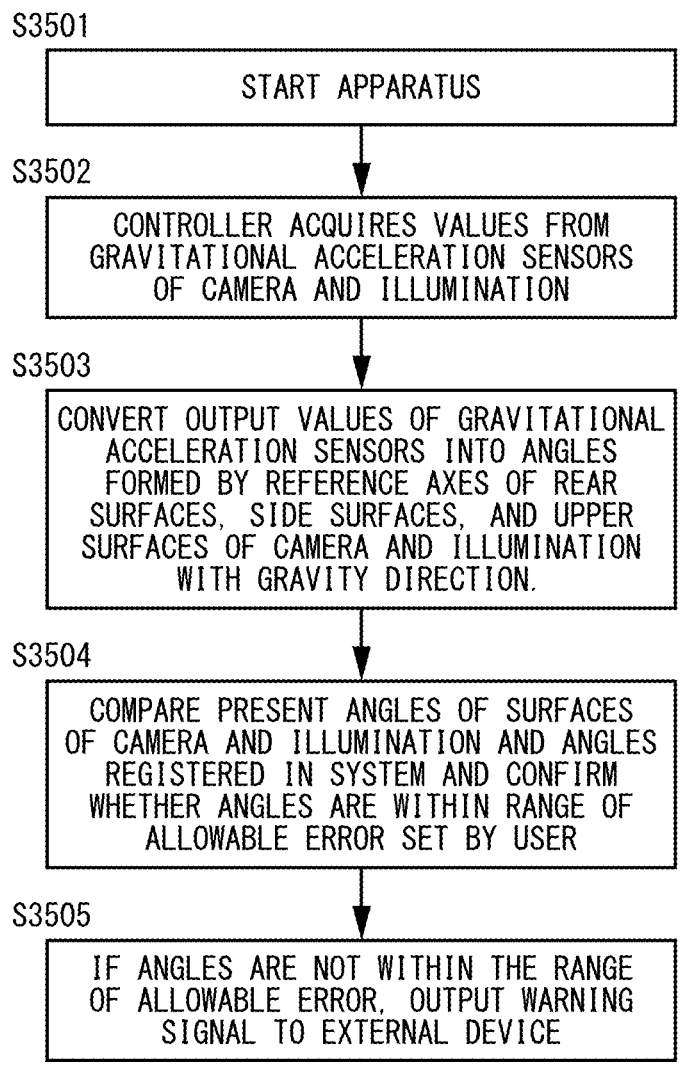
FIG. 35 is a flowchart for explaining a procedure for emitting a warning when the postures of the camera section and the illuminating section change.

The image inspection apparatus 100 includes a posture change warning function for, when the postures of the camera section and the illuminating section change because of some cause, for example, an unintended contact, vibration or a shock, or aged deterioration, detecting the change and emitting a warning. Therefore, the image inspection apparatus 100 includes a warning output section 35 as shown in FIG. 2. A procedure in which the warning output section 35 emits a warning when the postures of the camera section and the illuminating section change is explained with reference to a flowchart of FIG. 35. First, in step S3501, the image inspection apparatus is started. Note that timing when the warning function is operated may be set to timing such as timing when the inspection setting of the image inspection apparatus is switched, timing when the image inspection apparatus periodically polls a value, or timing when the camera periodically sends a value.

Subsequently, in step S3502, the image inspection apparatus acquires inclination values respectively from the gravitational acceleration sensors of the camera section and the illuminating section. In step S3503, the image inspection apparatus converts output values of the gravitational acceleration sensors into angles formed by the reference axes of the rear surfaces, the side surfaces, and the upper surfaces of the camera section and the illuminating section with the gravity direction.

Further, subsequently, in step S3504, the image inspection apparatus compares the present angles of the surfaces of the camera section and the illuminating section and the angles registered in the system and confirms whether the present angles are within a range of an allowable error set by the user.

Warning Condition Setting Field 144

A warning condition setting field 144 is provided in a lower part of the camera posture display screen 140 of the image inspection program shown in FIG. 27. The user designates, in advance, from the warning condition setting field 144, an allowable error range serving as a threshold for emitting a warning output. In a system variable allocation field 145, the user selects a value of which system variable is changed when an inclination error of the camera section and the illuminating section is detected. The user designates an error range allowable to a selected parameter from an angle allowable error field 146.

Further, timing when the warning output section determines whether warning conditions are satisfied can also be specified. In the example shown in FIG. 27 and the like, a confirmation timing setting field 147 is provided in the warning condition setting field 144. As determination timing of warning, a start time, an inspection setting reading time, and the like are enumerated. The user is capable of setting ON/OFF in checkboxes.

Lastly, in step S3505, if the angles are not within the range of the allowable error, the warning output section outputs a warning signal to the external control device 60. In this way, since the image inspection apparatus includes the posture change warning function, the image inspection apparatus can give a warning to the user when the postures of the camera section and the illuminating section change. It is possible to detect that a change occurs in the postures because of, for example, aged deterioration or a sudden shock and take appropriate processing such as repositioning.

Figure 36:
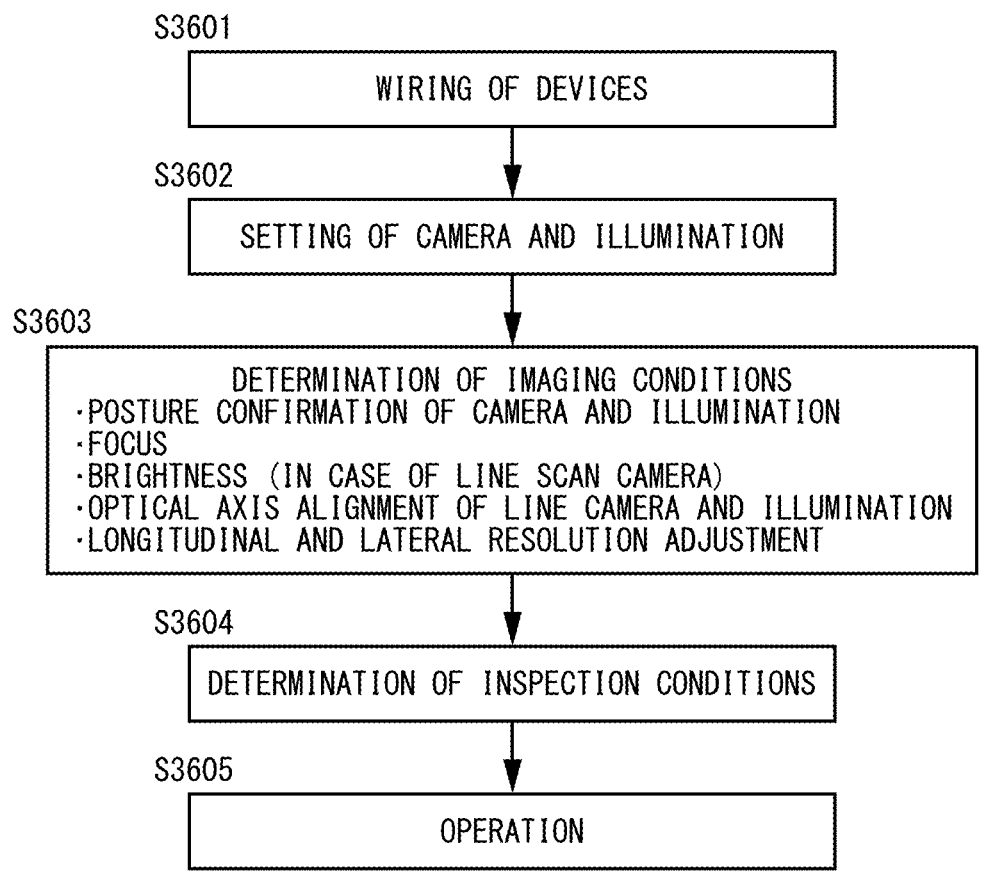
FIG. 36 is a flowchart for explaining a procedure performed when a posture change warning function is incorporated in a start of the image inspection apparatus.

Further, it is also possible to incorporate a function of displaying the postures of the camera section and the illuminating posture in a start time of the image inspection apparatus. Consequently, it is possible to confirm whether the postures of the camera section and the illuminating section are appropriate every time the image inspection apparatus is started. An example of such a procedure is explained on the basis of a flowchart of FIG. 36. First, in step S3601, wiring of the devises is performed. Subsequently, in step S3602, setting of the camera section and the illuminating section is performed. Further, subsequently, in step S3603, imaging conditions are determined. The determination of the imaging conditions includes posture confirmation of the camera section and the illuminating section and determination of a focus and brightness. In the case of the line camera, the determination of the imaging conditions includes optical axis alignment of the line camera and the illuminating section and longitudinal and lateral resolution adjustment. In step S3604, inspection conditions are determined. Lastly, in step S3605, operation is started. In this way, it is possible to perform the configuration and the fine adjustment of the setting of the camera section and the illuminating section every time the image inspection apparatus is started.

INDUSTRIAL APPLICABILITY

The image inspection apparatus, the image inspection method, the image inspection program, and the computer-readable recording medium or the device having the image inspection program recorded therein can be suitably used for a visual inspection of work conveyed on a line.

What is claimed is:

1. An image inspection apparatus for performing a visual inspection of an inspection target object, the image inspection apparatus comprising:
    an illuminating section for irradiating illumination light on the inspection target object;
    a line camera in which a plurality of imaging elements are arrayed to be linearly arranged, the line camera receiving the light irradiated from the illuminating section and reflected on the inspection target object;
    an image-for-optical-axis-adjustment generating section configured to repeatedly capture, with the line camera, images of an inspection target object for an optical axis adjustment in a standstill state to generate an image for the optical axis adjustment having periodicity in a line direction of the line camera;
    a display section for displaying an optical axis adjusting section for adjusting an optical axis of the line camera in a state in which the image for the optical axis adjustment generated by the image-for-optical-axis-adjustment generating section is displayed;
    a trigger setting section for specifying a trigger that specifies timing when the inspection target object is imaged by the line camera;
    an aspect ratio adjusting section for adjusting longitudinal and lateral pixel resolutions of the image captured by the line camera, wherein the aspect ratio adjusting section includes an image-for-pixel-resolution-calculation generating section for, after the optical axis adjustment of the line camera is performed on the basis of the image for the optical axis adjustment displayed on the display section, repeatedly capturing images with the line camera while moving, in one direction, a pattern for pixel resolution calculation having a known dimension to generate an image for a pixel resolution calculation, a pixel resolution calculation parameter setting section configured to set, as a pixel resolution calculation parameter, a ratio of the dimension measured by the measuring section and the actual dimension input to the dimension input section, and an interval adjusting section for adjusting an imaging interval of the line camera specified by the trigger setting section according to the pixel resolution calculation parameter set by the pixel resolution calculation parameter setting section; and
    an image-for-inspection generating section for repeating the imaging at the imaging interval adjusted by the interval adjusting section to generate an image for inspection.

2. The image inspection apparatus according to claim 1, wherein the aspect ratio adjusting section includes:
    a pixel resolution calculating section configured to calculate pixel resolutions in a longitudinal direction and a lateral direction of the image captured by the line camera; and
    an imaging parameter adjusting section for adjusting imaging parameters that define imaging conditions of the line camera.

3. The image inspection apparatus according to claim 2, wherein the aspect ratio adjusting section includes a longitudinal direction expansion and contraction section for expanding and contracting, in a longitudinal direction, the image obtained by the imaging of the line camera.

4. The image inspection apparatus according to claim 1, wherein the optical axis adjusting section is capable of adjusting an optical axis of the illuminating section.

5. The image inspection apparatus according to claim 1, wherein the aspect ratio adjusting section includes an interval adjusting section for adjusting an imaging interval of the line camera.

* * * * *